(12) United States Patent
Nadal Roura

(10) Patent No.: US 11,034,639 B2
(45) Date of Patent: Jun. 15, 2021

(54) METHODS OF PURIFYING CANNABINOIDS USING LIQUID:LIQUID CHROMATOGRAPHY

(71) Applicant: Phytoplant Research S.L., Cordova (ES)

(72) Inventor: Xavier Nadal Roura, Cordova (ES)

(73) Assignee: PHYTOPLANT RESEARCH S.L., Cordova (ES)

(*) Notice: Subject to any disclaimer, the term of this patent is extended or adjusted under 35 U.S.C. 154(b) by 0 days.

(21) Appl. No.: 16/295,220

(22) Filed: Mar. 7, 2019

(65) Prior Publication Data
US 2019/0201809 A1    Jul. 4, 2019

Related U.S. Application Data

(63) Continuation-in-part of application No. 16/239,002, filed on Jan. 3, 2019, which is a continuation-in-part of application No. 15/948,581, filed on Apr. 9, 2018, now Pat. No. 10,207,199, which is a continuation of application No. 15/882,516, filed on Jan. 29, 2018, now Pat. No. 10,207,198, which is a continuation-in-part of application No. 15/707,524, filed on Sep. 18, 2017, now Pat. No. 10,155,708, which is a continuation-in-part of application No. 15/004,848, filed on Jan. 22, 2016, now Pat. No. 9,765,000.

(60) Provisional application No. 62/106,644, filed on Jan. 22, 2015.

(51) Int. Cl.
| | | |
|---|---|---|
| B01D 11/02 | (2006.01) | |
| B01D 15/08 | (2006.01) | |
| C07D 311/80 | (2006.01) | |
| C07C 37/72 | (2006.01) | |
| B01D 15/18 | (2006.01) | |
| C07C 51/48 | (2006.01) | |
| B01D 11/04 | (2006.01) | |
| C07C 37/00 | (2006.01) | |
| G01N 30/88 | (2006.01) | |
| C07C 29/76 | (2006.01) | |
| B01D 15/42 | (2006.01) | |

(52) U.S. Cl.
CPC .......... *C07C 37/72* (2013.01); *B01D 11/0203* (2013.01); *B01D 11/0288* (2013.01); *B01D 11/0492* (2013.01); *B01D 15/08* (2013.01); *B01D 15/1807* (2013.01); *B01D 15/1892* (2013.01); *B01D 15/42* (2013.01); *C07C 29/76* (2013.01); *C07C 37/004* (2013.01); *C07C 51/48* (2013.01); *C07D 311/80* (2013.01); *G01N 30/88* (2013.01); *C07C 2601/16* (2017.05)

(58) Field of Classification Search
CPC ............ B01D 11/0288; B01D 11/0203; B01D 11/0492; B01D 15/08; B01D 15/1807; B01D 15/1892; B01D 15/42; C11B 3/10; C07C 29/74; C07C 37/004; C07C 51/47; C07C 37/82; C07D 311/80
See application file for complete search history.

(56) References Cited

U.S. PATENT DOCUMENTS

| | | | |
|---|---|---|---|
| 6,365,416 B1 * | 4/2002 | Elsohly | G01N 30/12 436/161 |
| 7,524,881 B2 | 4/2009 | Goodwin et al. | |
| 7,700,368 B2 * | 4/2010 | Flockhart | C07D 311/80 436/177 |
| 9,744,151 B2 | 8/2017 | Gutman et al. | |
| 9,765,000 B2 | 9/2017 | Nadal Roura | |
| 10,155,708 B2 | 12/2018 | Nadal Roura | |
| 2006/0167283 A1 * | 7/2006 | Flockhart | C07C 37/70 549/390 |
| 2009/0298930 A1 | 12/2009 | Gutman et al. | |
| 2017/0333503 A1 | 11/2017 | Ayres | |
| 2018/0036278 A1 * | 2/2018 | Rutz | C07D 311/80 |
| 2018/0147247 A1 | 5/2018 | Ivanov | |

FOREIGN PATENT DOCUMENTS

| | | |
|---|---|---|
| EP | 2044935 A1 | 4/2009 |
| GB | 2393182 A | 3/2004 |
| WO | 2004026802 A1 | 4/2004 |
| WO | 2004026857 A2 | 4/2004 |

(Continued)

OTHER PUBLICATIONS

Nian Ling et al., The separation and identification of Δ9-tetrahydrocannabinol in cannabis, Research for Chinese Patent Medicine, Dec. 31, 1985, pp. 29-30, vol. 8, Shanghai Institute of Pharmaceutical Industry (Thesis), Shanghai, China.

(Continued)

*Primary Examiner* — Yate' K Cutliff

(74) *Attorney, Agent, or Firm* — Tristan A. Fuierer; Olive Law Group, PLLC

(57) ABSTRACT

The present specification discloses methods of purifying one or more cannabinoids from a plant material using unique biphasic solvent systems and liquid-liquid chromatography as centrifugation partitioning chromatography (CPC) or counter current chromatography (CCC). The present specification also provides purified cannabinoids such as CBG, CBGA, CBGV, CBD, CBDA, CBDV, THC, THCA and THCV, compositions comprising one or more of these cannabinoids produced by the disclosed method, and methods for treating a disease or condition employing such purified cannabinoids and compositions.

19 Claims, No Drawings

(56) References Cited

FOREIGN PATENT DOCUMENTS

| WO | 2006053766 A1 | 5/2006 |
| WO | 2016187679 A1 | 12/2016 |

OTHER PUBLICATIONS

Arno Hazekemp et a., Preparative Isolation of Cannabinoids from Cannabis sativa by Centrifugal Partition chromatography, Journal of Liquid Chromatography & Related Technologies, Dec. 2004, pp. 39-52, Leiden Univeristy (Thesis), Leiden, The Netherlands.

Oka F. et al.; "Systematic search for suitable two-phase solvent systems for high-speed counter-current chromatography," Journal of Chromatography, 1991, No. 538, pp. 99-108.

* cited by examiner

METHODS OF PURIFYING CANNABINOIDS USING LIQUID:LIQUID CHROMATOGRAPHY

This application claims priority to and is a continuation-in-part of U.S. patent application Ser. No. 16/239,002, filed Jan. 3, 2019, which claims priority to and is a continuation-in-part of U.S. patent application Ser. No. 15/948,581, filed Apr. 9, 2018, now U.S. Pat. No. 10,207,199, which claims priority to and is a continuation of U.S. patent application Ser. No. 15/882,516, filed on Jan. 29, 2018, now U.S. Pat. No. 10,207,198, which claims priority to and is a continuation in part of U.S. patent application Ser. No. 15/707,524, filed Sep. 18, 2017, now U.S. Pat. No. 10,155,708, which claims priority to and is a continuation-in-part of U.S. patent application Ser. No. 15/004,848, filed on Jan. 22, 2016, now U.S. Pat. No. 9,765,000, which claims the benefit of U.S. Provisional Patent Application 62/106,644, filed on Jan. 22, 2015, the contents of which are each hereby incorporated by reference in their entirety.

TECHNICAL FIELD

The present invention relates to the isolation of cannabinoid compounds using unique biphasic solvent systems and liquid-liquid chromatography as centrifugation partitioning chromatography (CPC) or counter current chromatography (CCC).

BACKGROUND OF THE INVENTION

*Cannabis* is a genus of flowering plants whose species are distinguished by plant phenotypes and secondary metabolite profiles. *Cannabis* is a genus include: *Cannabis* sp. including *Cannabis sativa* L. and all subspecies, the putative species *Cannabis indica* Lam., *Cannabis ruderalis* Janisch, and hybrids and varieties thereof, as discussed further below. *Cannabis* plants have been cultivated for a variety of uses including making fibers (hemp), medicinal use and recreational drug use. *Cannabis* is also commonly known as marijuana.

*Cannabis* has now been generally acknowledged as having substantial benefits for various medical uses. For example, *cannabis* is regularly used by a wide cross-section of society to treat a variety of maladies, ailments and symptoms including, but not limited to, nausea, pain relief (such as chronic pain, cancer related pain, or neuropathic pain), glaucoma, lack of appetite, mucous membrane inflammation, inflammatory diseases (such as Crohn's disease), neurodegenerative disease, epilepsy (that affects children and adults), seizures, diabetes, leprosy, fever, obesity, asthma, urinary tract infections, coughing, anorexia associated with weight loss in AIDS patients, graft-versus-host disease, glioma, perinatal asphyxia and post-traumatic stress disorder (PTSD) and autoimmune disease (such as multiple sclerosis).

One of the most common ways that *cannabis* is used for medicinal use in many countries is through smoking. Smoking medical *cannabis*, although proven to be beneficial in certain indications, has disadvantages. For example, the amounts of active ingredients may differ depending on the differences present in plant varietals as well as changing growing conditions which result in intravarietal variations. As a result, it can be difficult to maintain control over the proper dosing of medicinal *cannabis* due to active ingredients fluctuations. Another disadvantage of smoking medical *cannabis* is the negative impact of some of the constituents of *cannabis* smoke. The smoke from the plant matter comprise carcinogens in addition to the desired cannabinoids. In addition, heavy *cannabis* use through smoking has been associated with accelerated pulmonary decline.

Cannabinoids are compounds active on cannabinoid receptors in humans and are responsible for eliciting many of the pharmacological effects of *cannabis*. Cannabinoids of plant origin, also known as phytocannabinoids, are abundant in *Cannabis*. Two known cannabinoids which are present in relatively high concentrations in *Cannabis sativa* L. are tetrahydracannabinolacid (THCA) or its decarboxylated product tetrahydracannabinol (THC) and cannabidiolic acid (CBDA) or its decarboxylated product cannabidiol (CBD). THC elicits psychoactive (calming) effects, analgesic effects, antioxidant effects and to increase appetite. However, THC is also associated with many negative or undesirable side effects including, but are not limited to, decreased short-term memory, dry mouth, impaired visual perception and motor skills, red (i.e., blood shot) eyes, increased anxiety, occasional infarction, stroke, paranoia, acute psychosis, lowered mental aptitude, hallucinations, bizarre behavior, irrational panic attacks, irrational thoughts and various other cognitive and social problems. On the other hand, CBD is increasingly becoming a popular cannabinoid for medicinal purposes because unlike THC, CBD is non-psychoactive at typical doses. In addition, CBD was found to have neuroprotective effects and to have ameliorative effects in patients with epilepsy, schizophrenia and Parkinson's disease. Accordingly, patients and healthcare providers are exhibiting a preference for CBD because patients need to work, drive and function with clarity while undergoing treatment.

Diverse chromatographic techniques have been used purify cannabinoid compounds from the plant *Cannabis sativa*. For example, Flash chromatography on silica gel, C8 or C18; preparative HPLC on silica gel columns, C8 or C18; and supercritical $CO_2$ chromatography on silica gel. However, these chromatographic processes are tedious and expensive.

Thus, what is needed is a simple and less expensive process that selectively purifies and concentrates medically beneficial cannabinoids. In addition, it is also desirous to develop medicinal formulations comprising higher levels of beneficial cannabinoids. However, THC and THCA can also be purified by this method from THC-THCA rich or THC-THCA low *Cannabis sativa* L. plant and extracts.

Centrifugation partitioning chromatography (CPC) and counter current chromatography (CCC) can be used, e.g., in the extraction and enrichment of compounds from plant extracts in analytical, semi-preparative and preparative scale. CPC and CCC are a liquid-liquid chromatography methods using a mostly two-phase solvent. It enables an almost loss-free separation of complex mixtures of substances from crude extracts. CPC and CCC as compared to liquid chromatography (HPLC) are easier and also cheaper, because matrix effects and irreversible adsorption on solid phases do not occur. Cannabinoids have been purified using CPC, but not using the solvent systems described in this patent application (see, e.g., Hazekamp, et al., "Preparative Isolation of Cannabinoids from *Cannabis sativa* by Centrifugal Partition Chromatography", Journal of Liquid Chromatography & Related Technologies, vol. 27, no. 15, 11 Jan. 2004 (2004-01-11), pages 2421-2439, XP055202081, ISSN: 1082-6076, DOI: 10.1081/JLC-200028170; see also WO2016/135346). These systems have long run times, less sample load and only moderate yields.

The present disclosure solves these and other problems by providing a method for isolating and purifying cannabinoid compounds using a solvent system and centrifugation partition chromatography (CPC) or counter current chromatography (CCC). In the case of CPC, there is significantly less time on the centrifuge and a large sample load, using the Quantum CPC rotor (ARMEN) or the CPC 1000 PRO (GILSON). By means of this procedure it is possible to obtain high yields of cannabinoid compounds having a purity of 95% or more.

SUMMARY OF THE INVENTION

In one aspect, the present invention provides a method of purifying one or more cannabinoids from a plant material including a plant, a plant resin or a plant extract, the method consisting essentially of the following steps:
  (a) incubating the plant material with a solvent selected from the group consisting of pentane, hexane, heptane, petroleum ethers, cyclohexane, dichloromethane, trichloromethane, tetrahydrofurane, diethyl ether, toluene, benzene, ethanol, methanol, isopropanol, acetone, acetonitrile, ethyl acetate, butane, propane, 1,1,1,2-Tetrafluoroethane (R134a) or, liquid, subcritical or supercritical $CO_2$ or mixes thereof to form a solvent mixture which extracts the one or more cannabinoids from the plant material, wherein the solvent mixture has an original volume;
  (b) for THC-type extracts, adding to the solvent mixture a biphasic solvent system selected from the group consisting of hexane:ethanol:water, pentane:acetonitrile and hexane:acetonitrile, wherein the pentane:acetonitrile system and the hexane:acetonitrile system optionally include ethyl acetate and/or water as a modifier; for CBD-type extracts, adding to the extract a biphasic sovent system of hexane:ethanol:water; and for CBG-type extracts, adding to the extract a biphasic solvent system of hexane:ethanol:water; and
  (c) performing liquid:liquid chromatography using a biphasic solvent system of step b), thereby purifying the one or more cannabinoids.

In one embodiment, for the THC-type extracts the biphasic solvent system is hexane:ethanol:water is at a ratio of (20:17:3) by volume. In another embodiment, for the THC-type extracts the biphasic solvent system is pentane:ethyl acetate:acetonitrile:water at a ratio from (10:0:10:0) to (7:3:7:3) by volume. In another embodiment, for the THC-type extracts the biphasic solvent system is hexane:ethyl acetate:acetonitrile:water at a ratio from (10:0:10:0) to (7:3:7:3) by volume. In another embodiment, for the CBD-type extracts the biphasic solvent system is hexane:ethanol:water at a ratio of (20:14:6) by volume. In another embodiment, for the CBG-type extracts the biphasic solvent system is hexane:ethanol:water at a ratio of at a ratio of (20:12:8) or (20:13:7) by volume.

In one embodiment, an extract of chemotype I or II *Cannabis sativa* L. is used to purify THC, THCA, THCV, THCVA, CBN or CBV and fractionate the CBD-type and CBG-type cannabinoids. In another embodiment, an extract of chemotype II or III *Cannabis sativa* L. is used to purify CBD, CBDA, CBDVA or CBDV and fractionate the THC-type and CBG-type cannabinoids. In another embodiment, an extract of chemotype IV *Cannabis sativa* L. is used to purify CBG, CBGA, CBGVA or CBGV and fractionate the CBD-type and THC-type cannabinoids.

In one embodiment, fractions of THC contaminated by CBC or the fractions of the THCV contaminated with CBN are re-purified using solid-liquid chromatography selected from the group consisting of gravity, Flash or preparative HPLC over C-8 or C-18 coated silica solid stationary phase, using a gradient of acetonitrile:water mobile liquid phase.

In one embodiment, the liquid:liquid chromatography is centrifugation partitioning chromatography (CPC) or is counter current chromatography (CCC).

In one embodiment, after step a) the solvent mixture is reduced to dryness or to about 50% or less of the original volume of the solvent mixture in step (a) thereby concentrating the one or more cannabinoids before the liquid:liquid chromatography.

In one embodiment, the solvent mixture of step (a) is purified prior to step (b). In another embodiment, prior to step (a), the one or more cannabinoids present in the plant material are decarboxylated by heating the plant material. In another embodiment, after the solvent mixture is reduced to dryness, a dry extract product of the solvent mixture is dissolved in ethanol, chilled at a temperature from −20° C. to 4° C., filtered to remove precipitated material and reduced to dryness before purification by liquid-liquid chromatography.

In one embodiment, the method of CPC uses a rotor design Quantum CPC or CPC PRO. In another embodiment, the method of CPC uses a rotor design Quantum CPC or CPC PRO, wherein the total run time is 12-20 minutes, independent of rotor volume. In another embodiment, the CPC rotor has a rotor volume of 1 liter, a sample injection of 50 mL, a flow rate of a mobile phase (pentane or hexane phase) of the biphasic solvent system of 200 mL/min during the run, and a flow rate of a stationary phase (the ethanolic or acetonitrile phase) of the biphasic solvent system of 350 mL/min during the extrusion phase of the run.

In one embodiment, the CBD, CBDA, CBDVA or CBDV is crystalized after the step of liquid:liquid chromatography. In another embodiment, the CBG, CBGA, CBGVA or CBGV is crystalized after the step of liquid:liquid chromatography.

In one embodiment, the plant material is first incubated with a non-polar solvent selected from the group consisting of petroleum ether, pentane, hexane and heptane to form a solvent mixture which extracts the one or more cannabinoids from the plant material to form the solvent mixture.

In one embodiment, the plant material is first incubated with a solvent selected from the group consisting of pentane, hexane, heptane, petroleum ethers, cyclohexane, dichloromethane, trichloromethane, tetrahydrofurane, diethyl ether, toluene, benzene, ethanol, methanol, isopropanol, acetone, acetonitrile, ethyl acetate, butane, propane, 1,1,1, 2-Tetrafluoroethane (R134a) or, liquid, subcritical or supercritical $CO_2$ or mixes thereof; filtered, decanted or centrifuged; reduced to dryness; and then incubated with a non-polar solvent selected from the group consisting of petroleum ether, pentane, hexane and heptane to form a solvent mixture which extracts the one or more cannabinoids from the plant material to form the solvent mixture.

In one embodiment, after step (a) the one or more cannabinoids present in the plant material and extracts are decarboxylated by heating the solvent mixture, wherein the solvent mixture is the original volume, a concentrated volume or a dry extract obtained from evaporation to dryness of the original volume of the solvent mixture.

In one embodiment, fractions of THC contaminated by CBC or the fractions of the THCV contaminated with CBN are re-purified using solid-liquid chromatography selected from the group consisting of gravity, Flash or preparative HPLC over C-8 or C-18 coated silica solid stationary phase, using a gradient of acetonitrile:water mobile liquid phase.

In one embodiment, the cannabinoid is selected from the group consisting of CBD, CBDA and CBDV. In another embodiment, the cannabinoid is selected from the group consisting of CBG, CBGA and CBGV. In another embodiment, the cannabinoid is selected from the group consisting of THC, THCA and THCV.

Other aspects of the present specification disclose methods of treating a disease or condition using purified cannabinoids and pharmaceutical compositions comprising one or more cannabinoid produced by the disclosed methods. Non-limiting examples of a disease or condition include pain, schizophrenia, convulsion, inflammation, anxiety, depression, neurodegenerative disease, stroke, traumatic brain injury, cancer, migraines, arthritis, chronic pain, nausea and vomiting, anorexia, glaucoma, glioma, epilepsy, asthma, perinatal asphyxia, graft-versus-host disease, addiction, symptoms of dependency and withdrawal, multiple sclerosis, spinal cord injury, Tourette's syndrome, dystonia, or tardive dyskinesia.

BRIEF DESCRIPTION OF THE DRAWINGS

Not applicable.

DETAILED DESCRIPTION OF THE INVENTION

The present invention provides a method for isolating and purifying one or more cannabinoids from a plant extract using liquid:liquid chromatography. Non-limiting examples of a cannabinoid include tetrahydrocannabinol (THC), tetrahydrocannabidivarin (THCV), tetrahydrocannabinolic acid (THCA), cannabidiol (CBD), cannabidivarin (CBDV), cannabidiolic acid (CBDA), cannabigerovarin (CBGV), cannabigerol (CBG), and cannabigerol acid (CBGA) from a plant belonging to the genus *Cannabis*.

Liquid:Liquid Chromatography

The disclosed method provides for purification of cannabinoids from a plant extract using a liquid:liquid chromatographic step. An optional crystallization step(s) may be performed before or after the step of liquid:liquid chromatorgraphy. Alternatively, no crystallization step is used, only the liquid:liquid chromatographic step. In one embodiment, the liquid:liquid chromatography step includes countercurrent chromatography or centrifugal partition chromatography. In an aspect of the chromatographic embodiment, the chromatographic step is applied after each crystallization step described below (e.g. after step (c), (e), (h) or (i)). In one embodiment the CPC/CCC chromatographic step is applied prior to the crystallization step described below (e.g., after step (b)).

Both CCC and CPC are liquid-liquid based chromatographic methods, where both the stationary phase and the mobile phase are liquids. By eliminating solid supports, permanent adsorption of the analyte onto the column is avoided, and a high recovery of the analyte can be achieved. The instrument is also easily switched between normal-phase and reversed-phase modes of operation simply by changing the mobile and stationary phases. With liquid chromatography, operation is limited by the composition of the columns and media commercially available for the instrument. Nearly any pair of immiscible solutions can be used in liquid-liquid chromatography provided that the stationary phase can be successfully retained. In one embodiment, the mobile phase is organic and/or non-polar, and the stationary phase is the aqueous and/or polar reagent.

Solvent costs for liquid:liquid chromatography are also generally lower than for high-performance liquid chromatography (HPLC), and the cost of purchasing and disposing of solid adsorbents is eliminated. Another advantage is that experiments conducted in the laboratory can be scaled to industrial volumes. When GC or HPLC is carried out with large volumes, resolution is lost due to issues with surface-to-volume ratios and flow dynamics; this is avoided when both phases are liquid.

In one embodiment, the mobile organic phase may include pentane, petroleum ether, hexane, cyclohexane, or heptane. In one embodiment, the stationary phase may include ethanol, methanol, isopropanol, acetone, acetonitrile and/or water. In one embodiment, the mobile phase is pentane, hexane, cyclohexane, or heptane and the stationary phase is water and ethanol, methanol, or isopropanol. In one embodiment, the mobile phase is pentane or heptane, and the stationary phase is acetone and/or acetonitrile with the possible use of water as a modifier.

In countercurrent chromatography (CCC) and centrifugal partition chromatography (CPC), a two-phase system is used. In one embodiment of the presently recited methods, the two-phase system hexane:ethanol:water used at ratios of (20:19:1) to (20:8:12). One embodiment uses ratios of (20:13:7) or 20:12:8 for isolation of CBG-type cannabinoids (CBG, CBGA, CBGVA and CBGV). One embodiment uses ratios of (20:14:6) for isolation of CBD-type cannabinoids (CBD, CBDA, CBDVA and CBDV). One embodiment uses ratios of (20:17:3) for isolation of THC-type cannabinoids (THC, THCA, THCVA and THCV). Substitutions of pentane, heptane and/or cyclohexane can be made for hexane and substitutions of methanol or isopropanol for ethanol.

One embodiment uses a gradient reverse phase run with an ethanol and water mix as the mobile phase and hexane as the stationary phase, increasing the concentration of ethanol gradually from the ratio (20:12:8) to (20:18:2), with substitutions of pentane, heptane and/or cyclohexane for hexane and methanol or isopropanol instead of ethanol.

In one embodiment the two phase system is pentane:acetonitrile or hexane:acetonitrile with or without ethyl acetate or water as a modifier for the isolation of THC-type cannabinoids. In one embodiment for THC-type extracts, the ratio of pentane:acetonitrile is from 10:10 to 7:3, e.g., pentane:ethyl acetate:acetonitrile:water (10:0:10:0) to pentane:ethyl acetate:acetonitrile:water (7:3:7:3) by volume. In another embodiment the ratio of hexane:acetonitrile is from 10:10 to 7:3, e.g., hexane:ethyl acetate:acetonitrile:water (10:0:10:0) to hexane:ethyl acetate:acetonitrile:water (7:3:7:3) by volume. Preferred solvent ratios for THC-type cannabinoids are pentane:ethyl acetate:acetonitrile:water at (19:1:19:1) by volume or (9:1:9:1) by volume. These two systems can also be used for CBD and CBG-type extracts. For CBD-type extracts the ratio of pentane:ethyl acetate:acetonitrile:water is preferably (8:2:8:2) by volume and for CBG-type extracts the ratio of pentane:ethyl acetate:acetonitrile:water is (7:3:7:3) by volume. Substitutions of pentane, heptane and/or cyclohexane can be made for hexane and substitutions of methanol or isopropanol can be made instead of ethanol Another embodiment of the present methods includes a two-phase system having hexane:ethanol:water at ratios ranging from (20:20:1) to (20:1:20) and from (20:1:5) to (20:1:10) and from (1:20:10) to (30:20:1). For example the ratio of hexane to ethanol may be range from about 1:20 to about 20:1, e.g., about 1:20, about 1:10, about 3:20, about 4:20, 5:20, about 6:20, about 7:20, about 8:20, about 9:20, about 10:20, about 11:20, about 12:20, about 13:20, about 14:20, about 15:20, about 16:20, about 17:20, about 18:20, about 19:20, about 20:20, about 20:19, about 20:18, about 20:17, about 20:16, about 20:15, about 20:14, about 20:13, about 20:12, about 20:11, about 20:10, about 20:9, about 20:8, about 20:7, about 20:6, about 20:5, about 20:4, about 20:3, about 20:2, or about 20:1. Similarly the ratio of ethanol to water, may range from about 20:1 to about 1:20, e.g., about 1:20, about 1:10, about 3:20, about 4:20, 5:20, about 6:20, about 7:20, about 8:20, about 9:20, about 10:20, about 11:20, about 12:20, about 13:20, about 14:20, about 15:20, about 16:20, about 17:20, about 18:20, about 19:20, about 20:20, about 20:19, about 20:18, about 20:17, about 20:16, about 20:15, about 20:14, about 20:13, about 20:12, about 20:11, about 20:10, about 20:9, about 20:8, about 20:7, about 20:6, about 20:5, about 20:4, about 20:3, about 20:2, or about 20:1.

In one aspect the ratio of hexane:ethanol:water is (20:19:1) to (20:8:12), and with substitutions of pentane, heptane and/or cyclohexane with hexane and methanol and/or isopropanol instead of ethanol, with the organic phase of pentane or hexane as mobile phase or the two-phases system. In particular, the ratios of the two-phase system hexane:ethanol:water are (20:13:7) for isolation of CBG-type cannabinoids, (20:14:6) for isolation of CBD-type cannabinoids and (20:17:3) to isolate THC-type cannabinoids or using a gradient reverse phase run with ethanol and water mix as mobile phase increasing the concentration of ethanol gradually from the ratio (20:12:8) to (20:18:2).

Another embodiment is the method of the invention, wherein the two-phase system, hexane:ethanol:water is used, and substitutions of pentane, heptane and/or cyclohexane with hexane and methanol and/or isopropanol instead of ethanol, with the organic phase of pentane or hexane as mobile phase in the chromatographic techniques of CPC and CCC for isolating and/or purifying the cannabinoids that are present in extracts made with pentane, hexane, heptane, petroleum ethers, cyclohexane, dichloromethane, trichloromethane, tetrahydrofurane, diethyl ether, toluene, benzene, ethanol, methanol, isopropanol, acetone, acetonitrile, ethyl acetate, butane, propane, refrigerant gases (e.g., 1,1,1,2-Tetrafluoroethane (R134a)) or, liquid, subcritical or supercritical $CO_2$ or mixes of these solvents from any variety and chemotype of the *Cannabis sativa* L. plant.

Therefore, an embodiment of the method of the invention includes before or after each crystallization step (e.g., after step (c), (e), (h) or (i) as shown below) a countercurrent chromatography (CCC) or a centrifugal partition chromatography (CPC) are carried out to isolate and purify the cannabinoids: tetrahydrocannabinol (THC), tetrahydrocannabidivarin (THCV), tetrahydrocannabinolic acid (THCA), tetrahydrocannabidivarinic acid (THCVA), cannabidiol (CBD), cannabidivarin (CBDV), cannabidiolic acid (CBDA), cannabidivarinic acid (CBDVA), cannabinol (CBN), cannabivarin (CBV), cannabigerovarin (CBGV), cannabigerol (CBG), cannabigerovarinic acid (CBGVA) and cannabigerol acid (CBGA).

Crystallization of Cannabinoids

In one embodiment, a method of purifying one or more cannabinoids from a plant material comprises a) incubating the plant material with a first non-polar solvent to form a first solvent mixture which extracts the one or more cannabinoids from a plant material; b) reducing the volume of the first solvent mixture to about 50% or less of the original volume of the first solvent mixture in step (a) in a manner that concentrates the one or more cannabinoids; c) incubating the reduced first solvent mixture in a manner that crystalizes the one or more cannabinoids; d) incubating the one or more crystalized cannabinoids with a second non-polar solvent to form a second solvent mixture; and e) incubating the second solvent mixture in a manner that crystalizes the one or more cannabinoids, thereby resulting in the purification of one or more cannabinoids. The disclosed methods further provide that the one or more crystalized cannabinoids of step (c) may be purified prior to step (d), using, e.g., filtration that results in a collection of a mother liquor. The mother liquor may be collected and incubated in a manner that crystalizes the one or more cannabinoids. Step (a) may be repeated one or more times. Steps (d) and (e) may be repeated one or more times until the purity of the one or more cannabinoids is 95% or more.

In one embodiment, a method of purifying one or more cannabinoids from a plant material comprises a) incubating the plant material with a first non-polar solvent to form a first solvent mixture which extracts the one or more cannabinoids from a plant material; b) filtering the first solvent mixture; c) reducing the volume of the first solvent mixture to about 50% or less of the original volume of the first solvent mixture in step (a) in a manner that concentrates the one or more cannabinoids; d) incubating the reduced first solvent mixture in a manner that crystalizes the one or more cannabinoids; e) purifying the one or more crystalized cannabinoids in step (d) using filtration that results in a collection of a mother liquor; f) incubating the one or more crystalized cannabinoids with a second non-polar solvent to form a second solvent mixture, wherein the second solvent mixture dissolves at least 50% of the one or more crystalized cannabinoids; g) incubating the second solvent mixture in a manner that crystalizes the one or more cannabinoids; and h) purifying the one or more crystalized cannabinoids of step (g) using filtration that results in a collection of a mother liquor, thereby resulting in the purification of one or more cannabinoids. The disclosed methods may further comprise: i) purifying the one or more crystalized cannabinoids using filtration that results in a collection of a mother liquor; and j) incubating the mother liquor in a manner that crystalizes the one or more cannabinoids. Step (a) may be repeated one or more times. Steps (i) and (j), steps (f) and (g) and steps (f), (g) and (h) may be repeated one or more times until the purity of the one or more cannabinoids is 95% or more.

In one embodiment, a method of purifying one or more cannabinoids from a plant material comprises a) incubating the plant material with a first non-polar solvent to form a first solvent mixture which extracts the one or more cannabinoids from a plant material; b) filtering the first solvent mixture; c) reducing by evaporation, the volume of the first non-polar solvent in the filtrate obtained in step (b); d) incubating the reduced first solvent mixture in a manner that crystalizes the one or more cannabinoids; e) removing the first non-polar solvent by vacuum filtering; f) further reducing the amount of first non-polar solvent from the filtrate of (e) by evaporation; g) incubating the one or more crystalized cannabinoids with a second non-polar solvent to form a second solvent mixture, wherein the second solvent mixture dissolves at least 50% of the one or more crystalized cannabinoids; h) incubating the second solvent mixture in a manner that crystalizes the one or more cannabinoids; i) removing the second non-polar solvent by vacuum filtering and saving the crystals obtained; and j) adding sufficient non-polar solvent per gram of cannabinoid to dissolve the crystals obtained in step (i) and recrystallizing.

Aspects of the present specification disclose, in part, incubating the plant material with a first non-polar solvent to form a first solvent mixture which extracts the one or more cannabinoids from a plant material. The extract obtained from a plant can be obtained by maceration in a non-polar solvent. A "non-polar solvent" as used herein includes a liquid non-polar solvent comprising lower $C_5$-$C_{12}$, or $C_5$-$C_8$ straight chain, or branched chain alkanes. Non-limiting examples of the non-polar solvent include pentane, hexane, petroleum ether (60-80° C. bp), cyclohexane, heptane, chloroform, benzene, toluene, or diethyl ether. In one embodiment, the non-polar solvent used in any one of or all of the present extraction steps is hexane. In one aspect of this embodiment, at least one of the extraction and/or purification steps for extraction of CBG and/or CBGA is performed with hexane. In another embodiment, the non-polar solvent used in any one of or all of the present extraction steps is pentane or petroleum ether (40-60° C. bp). In one aspect of this embodiment, one or more of the extraction and/or purification steps for extraction/purification of CBD is performed with pentane or petroleum ether (40-60° C. bp). In another embodiment, the non-polar solvent used in any one of or all of the present extraction steps is heptane. In one aspect of this embodiment, one or more of the extraction and/or purification steps for extraction/purification of THCA is performed with heptane.

Besides the particular non-polar solvent, extraction of the one or more cannabinoids from a plant material is a function of temperature, time and number of extraction steps. In aspects of this embodiment, incubating the plant material with a non-polar solvent occurs for a time period of, e.g., at least 5 minutes, at least 10 minutes, at least 15 minutes, for at least 30 minutes, for at least 45 minutes, for at least 1 hour, for at least 1.25 hours, for at least 1.5 hours, for at least 1.75 hours, for at least 2 hours, for at least 2.25 hours, for at least 2.5 hours, for at least 2.75 hours, for at least 3.0 hours, for at least 3.25 hours, for at least 4.5 hours, for at least 4.75 hours, or for at least 5.0 hours. In other aspects of this embodiment, incubating the plant material with a non-polar solvent occurs for a time period of, e.g., at most 5 hours, for at most 4.75 hours, for at most 4.5 hours, for at most 4.25 hours, for at most 4.0 hours, for at most 3.75 hours, for at most 3.5 hours, for at most 3.25 hours, for at most 3.0 hours, for at most 2.75 hours, for at most 2.5 hours, for at most 2.25 hours, for at most 2.0 hours, for at most 1.75 hours, for at most 1.5 hours, for at most 1.25 hours, for at most 1.25 hours, for at most 1.0 hours, for at most 45 minutes, for at most 30 minutes, or for at most 15 minutes. In yet other aspects of this embodiment, incubating the plant material with a non-polar solvent occurs for a time period of, e.g., about 15 minutes to about 5 hours, about 30 minutes to about 5 hours, about 45 minutes to about 5 hours, about 1 hour to about 5 hours, about 1 hour to about 4 hours, about 1 hour to about 3.5 hours, about 1 hour to about 3.0 hours, about 1 hour to about 2.25 hours, about 1 hour to about 2 hours, about 1 hour to about 1.75 hours, about 1 hour to about 1.5 hours, about 30 minutes to about 1.5 hours, about 30 minutes to about 1.25 hours, about 30 minutes to about 1 hour, about 45 minutes to about 1.75 hours, about 45 minutes to about 1.5 hours, about 45 minutes to about 1.25 hours, or about 45 minutes to about 1 hour.

In aspects of this embodiment, incubating the plant material with a non-polar solvent occurs at a temperature of, e.g., 0° C. or higher, 4° C. or higher, 8° C. or higher, 12° C. or higher, 16° C. or higher, 20° C. or higher or 24° C. or higher, 28° C. or higher, 32° C. or higher, 36° C. or higher, 40° C. or higher, 44° C. or higher, 48° C. or higher, 52° C. or higher, 56° C. or higher or 60° C. or higher. In other aspects of this embodiment, incubating the plant material with a non-polar solvent occurs at a temperature of, e.g., 0° C. or lower, 4° C. or lower, 8° C. or lower, 12° C. or lower, 16° C. or lower, 20° C. or lower, 24° C. or lower, 28° C. or lower, 32° C. or lower, 36° C. or lower, 40° C. or lower, 44° C. or lower, 48° C. or lower, 52° C. or lower, 56° C. or lower or 60° C. or lower. In other aspects of this embodiment, incubating the plant material with a non-polar solvent occurs at a temperature of, e.g., about 0° C. to about 4° C., about 0° C. to about 8° C., about 0° C. to about 12° C., about 0° C. to about 16° C., about 0° C. to about 20° C., about 0° C. to about 24° C., about 0° C. to about 28° C., about 0° C. to about 32° C., about 0° C. to about 36° C., about 0° C. to about 40° C., about 0° C. to about 44° C., about 0° C. to about 48° C., about 0° C. to about 52° C., about 0° C. to about 56° C., about 0° C. to about 60° C., about 4° C. to about 8° C., about 4° C. to about 12° C. about 4° C. to about 16° C., about 4° C. to about 20° C., about 4° C. to about 24° C., about 4° C. to about 28° C., about 4° C. to about 32° C., about 4° C. to about 36° C., about 4° C. to about 40° C., about 4° C. to about 44° C., about 4° C. to about 48° C., about 4° C. to about 52° C., about 4° C. to about 56° C., about 4° C. to about 60° C., about 8° C. to about 12° C., about 8° C. to about 16° C., about 8° C. to about 20° C., about 8° C. to about 24° C., about 8° C. to about 28° C., about 8° C. to about 32° C., about 8° C. to about 36° C., about 8° C. to about 40° C., about 8° C. to about 44° C., about 8° C. to about 48° C., about 8° C. to about 52° C., about 8° C. to about 56° C., about 8° C. to about 60° C., about 12° C. to about 16° C., about 12° C. to about 20° C., about 12° C. to about 24° C., about 12° C. to about 28° C., about 12° C. to about 32° C., about 12° C. to about 36° C., about 12° C. to about 40° C., about 12° C. to about 44° C., about 12° C. to about 48° C., about 12° C. to about 52° C., about 12° C. to about 56° C., about 12° C. to about 60° C., about 16° C. to about 20° C., about 16° C. to about 24° C., about 16° C. to about 28° C., about 16° C. to about 32° C., about 16° C. to about 36° C., about 16° C. to about 40° C., about 16° C. to about 44° C., about 16° C. to about 48° C., about 16° C. to about 52° C., about 16° C. to about 56° C., about 16° C. to about 60° C., about 20° C. to about 24° C., about 20° C. to about 28° C., about 20° C. to about 32° C., about 20° C. to about 36° C., about 20° C. to about 40° C., about 20° C. to about 44° C., about 20° C. to about 48° C., about 20° C. to about 52° C., about 20° C. to about 56° C., about 20° C. to about 60° C., about 24° C. to about 28° C., about 24° C. to about 32° C., about 24° C. to about 36° C., about 24° C. to about 40° C., about 24° C. to about 44° C., about 24° C. to about 48° C., about 24° C. to about 52° C., about 24° C. to about 56° C., about 24° C. to about 60° C., about 28° C. to about 32° C., about 28° C. to about 36° C., about 28° C. to about 40° C., about 28° C. to about 44° C., about 28° C. to about 48° C., about 28° C. to about 52° C., about 28° C. to about 56° C., about 28° C. to about 60° C., about 32° C. to about 36° C., about 32° C. to about 40° C., about 32° C. to about 44° C., about 32° C. to about 48° C., about 32° C. to about 52° C., about 32° C. to about 56° C., about 32° C. to about 60° C., about 36° C. to about 40° C., about 36° C. to about 44° C., about 36° C. to about 48° C., about 36° C. to about 52° C., about 36° C. to about 56° C., about 36° C. to about 60° C., about 40° C. to about 44° C., about 40° C. to about 48° C., about 40° C. to about 52° C., about 40° C. to about 56° C., about 40° C. to about 60° C., about 44° C. to about 48° C., about 44° C. to about 52° C., about 44° C. to about 56° C., about 44° C. to about 60° C., about 48° C. to about 52° C., about 48° C. to about 56° C., about 48° C. to about 60° C., about 52° C. to about 56° C., about 52° C. to about 60° C., or about 52° C. to about 60° C.

Aspects of the present specification disclose, in part, purifying the solvent mixture. In an aspect of this embodiment, the solvent mixture is purified by filtration.

Aspects of the present specification disclose, in part, reducing the volume of the solvent mixture in a manner that concentrates the one or more cannabinoids, by at least 50% of the original volume to dryness. In aspects of this embodiment, the volume of the first solvent mixture is reduced by evaporation. In aspects of this embodiment, the volume of the first solvent mixture is reduced by, e.g., 60% or less, 50% or less, 45% or less, 40% or less, 35% or less, 30% or less, 25% or less, 20% or less, 15% or less, 10% or less, 5% or less, 4% or less, 3% or less, 2% or less, or 1% or less of the original volume of the first solvent mixture used to extract the one or more cannabinoids from a plant material. In aspects of this embodiment, the volume of the first solvent mixture is reduced by, e.g., about 0.1% to about 5%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.1% to about 45%, about 0.1% to about 50%, about 0.5% to about 5%, about 0.5% to about 10%, about 0.5% to about 15%, about 0.5% to about 20%, about 0.5% to about 25%, about 0.5% to about 30%, about 0.5% to about 35%, about 0.5% to about 40%, about 0.5% to about 45%, about 0.5% to about 50%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60% or about 55% to about 60%.

Aspects of the present specification disclose, in part, incubating the reduced solvent mixture in a manner that crystalizes one or more cannabinoids. Generally, crystallization of the one or more cannabinoids in the reduced first solvent mixture is a function of temperature and time. In aspects of this embodiment, the reduced first solvent mixture is incubated at a temperature of, e.g., −70° C. or higher, −60° C. or higher, −50° C. or higher, −40° C. or higher, −30° C. or higher, −20° C. or higher or 0° C. or higher, 4° C. or higher, 8° C. or higher, 12° C. or higher, 16° C. or higher, 20° C. or higher, 24° C. or higher or 28° C. or higher. In other aspects of this embodiment, the reduced first solvent mixture is incubated at a temperature of, e.g., −70° C. or lower, −60° C. or lower, −50° C. or lower, −40° C. or lower, −30° C. or lower, −20° C. or lower or 0° C. or higher, 4° C. or lower, 8° C. or lower, 12° C. or lower, 16° C. or lower, 20° C. or lower, 24° C. or lower or 28° C. or lower. In yet other aspects of this embodiment, the reduced first solvent mixture is incubated at a temperature of, e.g., about −70° C. to about 40° C., −70° C. to about 30° C., −70° C. to about 20° C., −70° C. to about 10° C., −70° C. to about 0° C., −20° C. to about 40° C., −20° C. to about 30° C., −20° C. to about 20° C., −20° C. to about 10° C., −20° C. to about 0° C., about 0° C. to about 5° C., about 0° C. to about 10° C., about 0° C. to about 15° C., about 0° C. to about 20° C., about 0° C. to about 25° C., about 0° C. to about 4° C., about 0° C. to about 8° C., about 0° C. to about 12° C., about 0° C. to about 16° C., about 0° C. to about 20° C., about 0° C. to about 24° C., about 0° C. to about 28° C., about 4° C. to about 8° C., about 4° C. to about 12° C. about 4° C. to about 16° C., about 4° C. to about 20° C., about 4° C. to about 24° C., about 4° C. to about 28° C., about 8° C. to about 12° C., about 8° C. to about 16° C., about 8° C. to about 20° C., about 8° C. to about 24° C., about 8° C. to about 28° C., about 12° C. to about 16° C., about 12° C. to about 20° C., about 12° C. to about 24° C., about 12° C. to about 28° C., about 16° C. to about 20° C., about 16° C. to about 24° C., about 16° C. to about 28° C., about 20° C. to about 24° C., about 20° C. to about 28° C. or about 24° C. to about 28° C.

In aspects of this embodiment, the reduced first solvent mixture is incubated for a time period of, e.g., 1 hour or more, 2 hours or more, 3 hours or more, 4 hours or more, 5 hours or more, 6 hours or more, 7 hours or more, 8 hours or more, 9 hours or more, 10 hours or more, 12 hours or more, 14 hours or more, 16 hours or more, 18 hours or more, 20 hours or more, 22 hours or more, 24 hours or more, 28 hours or more, 32 hours or more, 36 hours or more, 40 hours or more, 44 hours or more, 48 hours or more, 52 hours or more, 56 hours or more, 60 hours or more, 64 hours or more, 68 hours or more, 72 hours or more, 76 hours or more, 80 hours or more, 84 hours or more, 88 hours or more, 92 hours or more or 96 hours or more. In other aspects of this embodiment, the reduced first solvent mixture is incubated for a time period of, e.g., 1 hour or less, 2 hours or less, 3 hours or less, 4 hours or less, 5 hours or less, 6 hours or less, 7 hours or less, 8 hours or less, 9 hours or less, 10 hours or less, 12 hours or less, 14 hours or less, 16 hours or less, 18 hours or less, 20 hours or less, 22 hours or less, 24 hours or less, 28 hours or less, 32 hours or less, 36 hours or less, 40 hours or less, 44 hours or less, 48 hours or less, 52 hours or less, 56 hours or less, 60 hours or less, 64 hours or less, 68 hours or less, 72 hours or less, 76 hours or less, 80 hours or less, 84 hours or less, 88 hours or less, 92 hours or less or 96 hours or less. In yet other aspects of this embodiment, the reduced first solvent mixture is incubated for a time period of, e.g., about 1 hour to about 12 hours, about 1 hour to about 24 hours, about 1 hour to about 36 hours, about 1 hour to about 48 hours, about 1 hour to about 60 hours, about 1 hour to about 72 hours, about 1 hour to about 84 hours, about 1 hour to about 96 hours, about 2 hours to about 12 hours, about 2 hours to about 24 hours, about 2 hours to about 36 hours, about 2 hours to about 48 hours, about 2 hours to about 60 hours, about 2 hours to about 72 hours, about 2 hours to about 84 hours, about 2 hours to about 96 hours, about 4 hours to about 12 hours, about 4 hours to about 24 hours, about 4 hours to about 36 hours, about 4 hours to about 48 hours, about 4 hours to about 60 hours, about 4 hours to about 72 hours, about 4 hours to about 84 hours, about 4 hours to about 96 hours, about 6 hours to about 12 hours, about 6 hours to about 24 hours, about 6 hours to about 36 hours, about 6 hours to about 48 hours, about 6 hours to about 60 hours, about 6 hours to about 72 hours, about 6 hours to about 84 hours, about 6 hours to about 96 hours, about 8 hours to about 12 hours, about 8 hours to about 24 hours, about 8 hours to about 36 hours, about 8 hours to about 48 hours, about 8 hours to about 60 hours, about 8 hours to about 72 hours, about 8 hours to about 84 hours, about 8 hours to about 96 hours, about 12 hours to about 24 hours, about 12 hours to about 36 hours, about 12 hours to about 48 hours, about 12 hours to about 60 hours, about 12 hours to about 72 hours, about 12 hours to about 84 hours, about 12 hours to about 96 hours, about 16 hours to about 24 hours, about 16 hours to about 36 hours, about 16 hours to about 48 hours, about 16 hours to about 60 hours, about 16 hours to about 72 hours, about 16 hours to about 84 hours, about 16 hours to about 96 hours, about 24 hours to about 36 hours, about 24 hours to about 48 hours, about 24 hours to about 60 hours, about 24 hours to about 72 hours, about 24 hours to about 84 hours, about 24 hours to about 96 hours, about 36 hours to about 48 hours, about 36 hours to about 60 hours, about 36 hours to about 72 hours, about 36 hours to about 84 hours, about 36 hours to about 96 hours, about 48 hours to about 60 hours, about 48 hours to about 72 hours, about 48 hours to about 84 hours, about 48 hours to about 96 hours or about 72 hours to about 96 hours.

Aspects of the present specification disclose, in part, purifying the one or more cannabinoids which are crystalized after incubation in the reduced solvent mixture. In an aspect of this embodiment, purification of the one or more crystalized cannabinoids is performed using filtration that results in a collection of a mother liquor.

Aspects of the present specification disclose, in part, incubating the one or more crystalized cannabinoids with a second non-polar solvent to form a second solvent mixture. Incubation of the one or more crystalized cannabinoids with a second non-polar solvent to form a second solvent mixture at least partially dissolves the one or more crystalized cannabinoids. In aspects of this embodiment, incubation of the one or more crystalized cannabinoids with a second non-polar solvent to form a second solvent mixture dissolves, e.g., at least 50%, at least 55%, at least 60%, at least 65%, at least 70%, at least 75%, at least 80%, at least 85%, at least 90% or at least 95% of the one or more crystalized cannabinoids. In other aspects of this embodiment, incubation of the one or more crystalized cannabinoids with a second non-polar solvent to form a second solvent mixture dissolves, e.g., at most 50%, at most 55%, at most 60%, at most 65%, at most 70%, at most 75%, at most 80%, at most 85%, at most 90% or at most 95% of the one or more crystalized cannabinoids. In yet other aspects of this embodiment, incubation of the one or more crystalized cannabinoids with a second non-polar solvent to form a second solvent mixture dissolves, e.g., about 50% to about 95%, about 55% to about 95%, about 60% to about 95%, about 65% to about 95%, about 70% to about 95%, about 75% to about 95%, about 80% to about 95%, about 85% to about 95%, about 90% to about 95%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100% or about 95% to about 100%.

Aspects of the present specification disclose, in part, purifying the one or more crystalized cannabinoids obtained from a second solvent mixture, as described above for the solvent mixture. In an aspect of this embodiment, the one or more crystalized cannabinoids is purified using filtration that results in a collection of a mother liquor.

The disclosed methods may further comprise, incubating the mother liquor in a manner that crystalizes the one or more cannabinoids. The one or more cannabinoids can be crystalized using the same temperature and time conditions used to crystalizes the one or more cannabinoids from the reduced solvent mixture described above.

The result of the disclosed methods is a substantially pure preparation of one or more cannabinoids. A "substantially pure" preparation of a cannabinoid or a cannabinoid acid is defined as a preparation having a chromatographic purity (of the desired cannabinoid or cannabinoid acid) of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

In an aspect of this embodiment, the disclosed methods result in the purification of CBGA having a purity that is 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard. In an aspect of this embodiment, the disclosed methods result in the purification of CBG having a purity that is 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard. In an aspect of this embodiment, the disclosed methods result in the purification of CBD having a purity that is 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

The term "crude cannabinoid", "raw cannabinoid" or "product enriched in a given cannabinoid" encompasses preparations having at least 60%, at least 65%, at least 70%, at least 75%, at least 80%, at least 85%, or at least 90% chromatographic purity for the desired cannabinoid. Such a product will generally contain a greater proportion of impurities, non-target materials and other cannabinoids than a "substantially pure" preparation.

Cannabinoids

The cannabinoids purified by the disclosed methods are not particularly limited and include cannibigerol-type (CBG-type) cannabinoids; cannaibichromene-type cannabinoids (CBC-type); cannabidiol-type cannabinoids (CBD-type); tetrahydracannabinol-type cannabinoids (THC-type); cannabinol-type cannabinoids (CBN-type); and derivatives thereof. The cannabinoid derivatives may not themselves be cannabinoids. However, their chemistry is recognized as being derived from cannabigerol, cannabinol, or cannabidiol. For instance, cannabinoids of interest include the following and their corresponding acids: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), THC (tetrahydrocannabinol), CBT (Cannabicitran-type), Iso-THC (Iso-Tetrahydrocannabinol-type) and CBE (Cannabielsoin-type). In fresh plant material of *Cannabis*, most cannabinoids are present in the form carboxylic acid known as acidic cannabinoids or "cannabinoid acids". The free phenolic forms of the cannabinoids are also known as neutral cannabinoids.

The disclosed methods may be used to extract/purify cannabinoids or cannabinoid acids from any plant material known to contain such cannabinoids or cannabinoid acids. The source for the cannabinoids is not limited, but can include plant material. The term "plant material" encompasses a plant or plant part (e.g. bark, wood, leaves, stems, roots, flowers, fruits, seeds, berries or parts thereof) as well as exudates, resins, and plant extracts, and includes material falling within the definition of "botanical raw material" in the Guidance for Industry Botanical Drug Products Draft Guidance, August 2000, US Department of Health and Human Services, Food and Drug Administration Centre for Drug Evaluation and Research.

The disclosed methods may be used to extract/purify cannabinoids or cannabinoid acids from any plant material known to contain such cannabinoids or cannabinoid acids. Most typically, but not necessarily, the "plant material" will be derived from one or more *cannabis* plants. Plants from which cannabinoids may be isolated include: *Cannabis* sp. including *Cannabis sativa* L. and all subspecies, the putative species *Cannabis* indica Lam., *Cannabis ruderalis* Janisch, and hybrids and varieties thereof, as discussed further below. The *Cannabis sativa* L. plant can be of the variety Carma, Aida, Octavia, Juani or any other variety of the chemotype IV, whose main cannabinoid is CBG or CBGA (Meijer E P, Hammond K M. The inheritance of chemical phenotype in *Cannabis sativa* L. (II): Cannabigerol predominant plants. Euphytica. 2005. 145: 189-198) or from any variety belonging to the chemotype II or III, whose main cannabinoid is CBD or CBDA or even from a variety from the chemotype I, whose main cannabinoid is THC or THCA (de Meijer E P, Bagatta M, Carboni A, Crucitti P, Moliterni V M, Ranalli P, Mandolino G. The inheritance of chemical phenotype in *Cannabis sativa* L. Genetics. 2003. January; 163(1):335-46.)

In one embodiment, the disclosed methods use material from the plant *Cannabis sativa* L. variety belonging to chemotype IV, having CBGA/CBG as main cannabinoids. In another embodiment, the disclosed methods use material from the plant *Cannabis sativa* L. variety belonging to chemotype III, having CBDA/CBD as main cannabinoids. In another embodiment, the disclosed methods use material from the plant *Cannabis sativa* L. variety belonging to chemotype II, having THCA-CBDA/THC-CBD as main cannabinoids. In yet another embodiment, the disclosed methods use material from the plant *Cannabis sativa* L. variety belonging to chemotype I, having THCA/THC as the main cannabinoids.

The term "*cannabis* plant(s)" encompasses wild type *Cannabis sativa* and also variants thereof, including *cannabis* chemovars (varieties characterised by virtue of chemical composition) which naturally contain different amounts of the individual cannabinoids, also *Cannabis sativa* L. subspecies indica including the variants var. indica and var. kafiristanica, *Cannabis* indica and also plants which are the result of genetic crosses, self-crosses or hybrids thereof. The term "*cannabis* plant material" is to be interpreted accordingly as encompassing plant material derived from one or more *cannabis* plants. For the avoidance of doubt, it is hereby stated that "*cannabis* plant material" includes herbal *cannabis* and dried *cannabis* biomass.

"Decarboxylated *cannabis* plant material" refers to *cannabis* plant material which has been subject to a decarboxylation step in order to convert cannabinoid acids to the corresponding free cannabinoids.

Resins and Extracts

"Resin" as used herein includes resins produced from any of the plant types discussed above, and in one embodiment, includes products of the stalked resin glands of *Cannabis* sp., including the putative species *Cannabis* indica, the species *Cannabis sativa* and *Cannabis ruderalis*, and hybrids or varietals thereof. These stalked resin glands may be from female, unfertilized or fertilized plants or from dioecious or monoecious varieties of *Cannabis*.

The method of the invention makes it possible to isolate the cannabinoids of interest (e.g., CBG, CBGA, CBGVA, CBD, CBDA, CBDVA, THC, THCA or THCVA) by crystallization with a non-polar solvent (e.g., hexane, pentane, heptane or petroleum ethers), from the plant, resin or the extracts obtained from the plant, wherein the crystallization is before or after a liquid:liquid chromatography step. In some cases, the extract of the resin or plant is first obtained by extracting with pentane, hexane, heptane, petroleum ethers, cyclohexane, dichloromethane, trichloromethane, tetrahydrofurane, diethyl ether, toluene, benzene, ethanol, methanol, isopropanol, acetone, acetonitrile, ethyl acetate, butane, propane, refrigerant gases (e.g.: 1,1,1,2-Tetrafluoroethane (R134a)) or, liquid, subcritical or supercritical $CO_2$ or mixes of these solvents. In this embodiment, the disclosed method obtains the cannabinoids of interest (e.g., CBG, CBGA, CBGVA, CBD, CBDA, CBDVA, THC, THCA or THCVA) with a purity of 60% to 96%, which will be called "raw" with a high yield and further with a purity of at least 60%, at least 61%, at least 62%, at least 63%, at least 64% at least 65%, at least 66%, at least 67%, at least 68%, at least 69%, least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 94% or at least 95% (the yield ranges between 50%-90% depending on the type of plant raw material or the type of extract). With subsequent recrystallizations of this "raw" composition in a non-polar solvent (e.g., hexane, pentane, heptane or petroleum ethers), it is possible to obtain a purity greater than 90%, greater than 91%, greater than 92%, greater than 93%, greater than 94%, greater than 95%, greater than 96%, greater than 97%, greater than 98%, greater than 99%, of e.g., CBG, CBGA, CBGVA, CBD, CBDA, CBDVA, THC, THCA or THCVA.

The non-polar solvent used to obtain an extract is not particularly limited, the method of the invention offers good results with extracts obtained with any of pentane, hexane, heptane, cyclohexane, petroleum ethers, dichloromethane, trichloromethane, tethrahydrofurane, toluene, benzene, diethyl ether, ethanol, methanol, isopropanol, acetone, acetonitrile, ethyl acetate, butane, propane, refrigerant gases (e.g.: 1,1,1,2-Tetrafluoroethane (R134a)) and liquid, subcritical or supercritical $CO_2$ or mixes of these solvents.

Isolation of Cannabinoid Acids

In embodiments where the method is to be used for the isolation of cannabinoid acids, an acidified extraction solvent to prepare the initial extract may optionally be used to ensure the extraction of high levels of cannabinoid acids. The primary purpose of this acidification is to prevent/ minimise ionisation of the cannabinoid acid, which could otherwise adversely affect the purification process. In one embodiment, the method uses acidified non-polar solvents, of the types described above. Acidification may be achieved by the addition of a small volume of acid to the solvent. Generally, it is sufficient to add a relatively weak acid, such as acetic acid. For any given purification process the optimal amount and type of acid used may be determined empirically. An example of an acidified solvent is 0.1% acetic acid in hexane. Other solvents include pentane, hexane, heptane, cyclohexane, petroleum ethers, dichloromethane, trichloromethane, tethrahydrofurane, diethyl ether, ethanol, methanol, isopropanol, acetone, acetonitrile, ethyl acetate, butane, propane, refrigerant gas 1,1,1,2-Tetrafluoroethane (R134a), liquid $CO_2$, subcritical $CO_2$ or supercritical $CO_2$ or mixes of these solvents. This is the extraction solvent of choice for preparing an initial extract from the starting plant material in the preparation of cannabinoid acids.

Isolation of Cannabigerol, Cannabidiol or Tetrahydrocannabinol-Prior Decarboxylation In embodiments of the method where it is desired to purify free cannabinoids, rather than the cannabinoid acids, the plant material may be subjected to a decarboxylation step. The purpose of the decarboxylation step is to convert cannabinoid acids present in the plant material to the corresponding free cannabinoids. Decarboxylation may be carried out by heating the plant material to a defined temperature for a suitable length of time. Decarboxylation of cannabinoid acids is a function of time and temperature, thus at higher temperatures a shorter period of time will be taken for complete decarboxylation of a given amount of cannabinoid acid. In selecting appropriate conditions for decarboxylation consideration must, however, be given to minimizing thermal degradation of the desirable, pharmacological cannabinoids into undesirable degradation products, particularly thermal degradation of $\Delta^9$ THC to cannabinol (CBN).

Thus, in another embodiment of the present methods, cannabinoids, e.g., CBG, CBGA, CBGV, CBD, CBDA, CBDV, THC, THCA or THCV are isolated and purified, and in which prior to performing step (a), the plant material, resin or extracts from the plant are decarboxylated for at least about 1 hour, 1.1 hours, 1.2 hour, 1.3 hours, 1.4 hours, 1.5 hours, 1.6 hours, 1.7 hours, 1.8 hours, 1.9 hours, 2 hours, 2.1 hours, 2.2 hours, 2.3 hours, 2.4 hours, 2.5 hours, 2.6 hours, 2.7 hours, 2.8 hours, 2.9 hours, 3 hours, 3.1 hours, 3.2 hours, 3.3 hours, 3.4 hours, 3.5 hours, 4 hours, 4.5 hours, 5 hours, 5.5 hours, 6 hours, 6.5 hours, 7 hours, 7.5 hours, 8 hours at around 60° C., 65° C., 70° C., 75° C., 80° C., 85° C., 90° C., 95° C., 100° C., 105° C., 110° C., 111° C., 112° C., 113° C., 114° C., 115° C., 116° C., 117° C., 118° C., 119° C., 120° C., 121° C. 122° C., 123° C., 124° C., 125° C., 126° C., 127° C., 128° C., 129° C. or 130° C., 135° C., 140° C., 145° C., 150° C., 155° C., 160° C., 165° C., 170° C., 175° C., or 180° C. In one embodiment, the decarboxylation is performed for at least 2 hours at a temperature of 120° C. In one embodiment, the decarboxylation is performed for at least 1 hours at a temperature of 150° C.

In one embodiment, the decarboxylation is performed at a temperature of at least 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., or 180° C. In one embodiment, the decarboxylation is performed at a temperature of at most 175° C., 170° C., 165° C., 160° C., 155° C., 150° C., 145° C., 140° C., 135° C., 130° C., 125° C., 120° C., 115° C., 110° C., 100° C., 95° C., 90° C., 85° C., 80° C., 75° C., 70° C., 65° C., or 60° C. In one embodiment, the decarboxylation is performed at a temperature ranging from 60° C. to 180° C., ranging from 70° C. to 175° C., 75° C. to 170° C., 80° C. to 165° C., 85° C. to 160° C., 90° C. to 155° C., 95° C. to 150° C., 100° C. to 145° C., 105° C. to 140° C., 110° C. to 135° C., 115° C. to 130° C., or 120° C. to 130° C.

Another embodiment is the method, wherein cannabigerol (CBG), cannabidiol (CBD), cannabidivarin (CBDV), tetrahydrocannabinol (THC), tetrahydrocannabidivarin (THCV), cannabinol (CBN), cannabivarin (CBV) and/or cannabigerovarin (CBGV) are isolated and purified, and in which prior to performing step (a), the plant material or resin of said plant are decarboxylated at least at 120° C. for 2 hours.

Another embodiment is the method, wherein step (a) is repeated at least once. In one embodiment, step (a) is repeated 2 times or 3 times. Another embodiment is the method, wherein time in step (a) is at least about 60 minutes.

Another embodiment is the method, wherein step (i) is repeated at least once. In one embodiment, step (i) is repeated 2 times or 3 times.

Characterization of Resultant Product

In one embodiment, the present methods obtain a substantially pure cannabinoid product. A "substantially pure" preparation of a cannabinoid or a cannabinoid acid is defined as a preparation having a chromatographic purity (of the desired cannabinoid or cannabinoid acid) of greater than 90%, greater than 91%, greater than 92%, greater than 93%, greater than 94%, greater than 95%, greater than 96%, greater than 97%, greater than 98%, greater than 99% and greater than 99.5%, as determined by area normalisation of an HPLC profile or by quantification by HPLC with a certified commercial standard.

Purity of CBG, CBGA, THC, THCA, THCV, CBDA, CBDV and CBD are expressed as HPLC quantification with certified commercial standard from Sigma-Aldrich. To evaluate the purity of CBGV we used the relative area by GCMS instrument, using the EIC (extractor ion chromatography) chromatogram to guarantee the correct measurement.

The HPLC conditions used to test the cannabinoid purity where the following: Column: Mediterranean Sea, C18, 3 μm size particle, 250 mm×4.6 mm; Mobil phase: Water and Methanol with formiate ammonium; Det.: DAD, 210 nm (CBG and CBD) and 270 nm (CBGA); 10 μL; Oven: 34° C.

Products Obtained by Methods

The present methods obtain a composition which includes a substantially pure cannabinoid or cannabinoid acid in liquid or solid form. For instance, the final product may be applied while in its crystalline form or may be further dissolved or formulated into a liquid, powder or compressed tablet. In one embodiment, the present methods obtain a crystalline cannabinoid in powder form. In another embodiment, the present methods obtain a cannabinoid solution.

The product obtained herein may be incorporated or formulated into products suitable for pharmaceutical purposes, recreational ingestion (e.g., food supplements, nutriceuticals), or as recreational inhalants (e.g., cigarettes and/or oils or liquids for electronic cigarettes/vape/hookah products, or incense).

Of course, working with *cannabis* plants and cannabinoids may require a government license or approval in some territories, but may often be obtained for medicinal purposes. That said, the present methods do not exclude the use of the product as a non-medicinal product, with the appropriate government approvals.

Pharmaceutical Product

The present methods in one embodiment produce a product which may be included in a pharmaceutical product, medicinal preparation, or medicament (hereinafter "pharmaceuticals"). Such pharmaceutical products may be formulated as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc.

Products obtained by the present methods may be included in a pharmaceutical composition including a compound of the present product or a pharmaceutically acceptable salt or solvate thereof, together with a pharmaceutically acceptable excipient. In an aspect of this embodiment, a pharmaceutical composition comprises CBGA, CBG, CBGV, CBDA, CBD, CBDV, THCA, THC, THCV or any combination thereof.

The term "excipient" is used herein to describe any ingredient other than the compound of the invention. The choice of excipient will to a large extent depend on factors such as the particular mode of administration, the effect of the excipient on solubility and Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nanoparticulates, gels, solid solutions, liposomal preparations, microencapsulated preparations, creams, films, ovules, suppositories and sprays.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form.

In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight % or from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets", Vol. 1, by H. Lieberman and L. Lachman (Marcel Dekker, New York, 1980).

Consumable oral films are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. The products obtained by the present methods can also be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile, pyrogen-free water.

Formulations for parenteral administration may be formulated to be immediate and/or modified release. Modified release formulations include delayed-, sustained-, pulsed-, controlled-, targeted and programmed release. Thus the compound of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds obtained by the present methods may also be administered topically to the skin or mucosa, that is, dermally or transdermally. Typical formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

The pharmaceutical composition described herein may be combined with the administration of another drug or active ingredient. Thus, the present products may be used to alleviate, minimize or prevent not only a disease or condition, but a side effect of another treatment regime.

Recreational Products

In one embodiment, the purified cannabinoids obtained by the present methods may be included in compositions such as oils (both for topical administration as massage oil, or to be burned or aerosolized), incense, cosmetics, bath oils, perfumes, makeup, food seasonings, toothpastes, ingestible solids (e.g., as a powder included in or on foods) or liquids (e.g., teas), etc.

For instance, a product produced by the present methods may be included in a "vape" product containing propylene glycol, glycerine, vegetable glycerine, aqueous glycerine, and optionally flavorings. In one aspect, the "vape" product may also include other drugs, such as nicotine.

Methods of Treating a Condition

The pharmaceutical products described herein may be administered to treat or reduce the symptoms of a disease or condition. In one embodiment, the present products may be administered to treat pain, Schizophrenia, convulsion, inflammation, anxiety or panic, depression (including unipolar or bipolar mood disorder and syndromal depression etc.), as a neuroprotective (i.e., for treatment of neurodegenerative disease, stroke, traumatic brain injury), cancer, graft-versus-host disease, migraines, arthritis, chronic pain (including neuropathic pain), nausea and vomiting, anorexia, glaucoma, glioma, epilepsy (that affects children and adults), asthma, perinatal asphyxia, addiction (and symptoms of dependency and withdrawal), movement disorders evidencing spasticity (in multiple sclerosis and spinal cord injury), Tourette's syndrome, dystonia, and tardive dyskinesia.

In particular methods embodiments, treatment methods reduce, decrease, suppress, limit, control or inhibit the presence of one or more symptoms associated with a condition; reduce, decrease, suppress, limit, control or inhibit side-effects of another pharmaceutical treatment; reduce, decrease, suppress, limit, control or inhibit the symptoms of addiction. In additional particular methods embodiments, treatment methods include administration of an amount of the present product sufficient to increase, induce, enhance, augment, promote or stimulate an immune response against the condition; or decrease, reduce, inhibit, suppress, prevent, control, or limit the spread of the condition within a subject or patient, or between subjects or patients. In further particular methods embodiments, treatment methods include administration of an amount of the present products sufficient to protect an individual from a pathology related to the condition, or reduce, decrease, limit, control or inhibit susceptibility to a pathology related to the condition.

Reagents for the Performance of the Present Method

In yet another embodiment the present invention includes reagents for the purification of cannabinoids. Such reagents include hexane (for CBG and CBGA), pentane and petroleum ether 40-60° C. bp (for CBD), heptane and petroleum ether 60-80° C. bp (for THCA) for the crystallization of the cannabinoid, and optionally reagents for the liquid chromatography such as ethanol, methanol, or isopropyl, or heptane, acetone, and acetonitrile.

Aspects

Aspects of the present specification can also be described as follows:

1. A method of purifying one or more cannabinoids from a plant material, the method comprising a) incubating the plant material with a first non-polar solvent to form a first solvent mixture which extracts the one or more cannabinoids from a plant material; b) reducing the volume of the first solvent mixture to about 50% or less of the original volume of the first solvent mixture in step (a) in a manner that concentrates the one or more cannabinoids; c) incubating the reduced first solvent mixture at a temperature range of between about −70° C. to about 40° C. in a manner that crystalizes the one or more cannabinoids; d) incubating the one or more crystalized cannabinoids with a second non-polar solvent to form a second solvent mixture, wherein the second solvent mixture dissolves at least 50% of the one or more crystalized cannabinoids; and e) incubating the second solvent mixture at a temperature range of between about −70° C. to about 40° C. in a manner that crystalizes the one or more cannabinoids, thereby resulting in the purification of one or more cannabinoids.
2. The method according to embodiment 1, wherein the plant material is a plant extract or a plant resin.
3. The method according to embodiment 1 or embodiment 2, wherein the plaint material is derived from the genera *Cannabis*.
4. The method according to any one of embodiments 1-3, wherein the plaint material is derived from a *Cannabis sativa* L, *Cannabis* indica *Cannabis ruderalis*, hybrids thereof or varietals thereof.
5. The method according to embodiment 4, wherein the *Cannabis sativa* L. varietal comprises a Chemotype I varietal, Chemotype II varietal, a Chemotype III varietal or a Chemotype IV varietal.
6. The method according to embodiment 4, wherein the *Cannabis sativa* L. varietal comprises a Carma varietal, a AIDA varietal, a SARA varietal, a PILAR varietal, a Futura 75 varietal, MONIEK varietal, or a 60.2/1/9 experimental varietal.
7. The method according to any one of embodiments 1-6, wherein prior to step (a), the plant material is treated to decarboxylate one or more cannabinoids present in the plant material.
8. The method according to any one of embodiments 1-7, wherein the first non-polar solvent of step (a) comprises pentane, hexane, heptane, cyclohexane, petroleum ether, dicloromethane, tricloromethane, tethrahydrofurane, diethyl ether, ethanol, methanol, isopropanol, acetone, acetonitrile, ethyl acetate, butane, propane, refrigeration gas 1,1,1,2-Tetrafluoroethane (R134a), liquid $CO_2$, subcritical $CO_2$ and supercritical $CO_2$.
9. The method according to any one of embodiments 1-8, wherein the one or more cannabinoids comprise tetrahydrocannabinol (THC), tetrahydrocannabidivarin (THCV), tetrahidrocannabinolic acid (THCA), tetrahydrocannabidivarinic acid (THCVA), cannabinol (CBN), cannabivarin (CBV), cannabidiol (CBD), cannabidivarin (CBDV), cannabidiolic acid (CBDA), cannabidivarinic acid (CBDVA), cannabigerol (CBG), canabigerovarin (CBGV), canabigerovarinic acid (CBGV) or cannabigerolic acid (CBGA).
10. The method according to any one of embodiments 1-9, wherein in step (a) the first solvent mixture is incubated at least 5 minutes.
11. The method according to embodiment 10, wherein in step (a) the first solvent mixture is incubated at about 10 minutes to about 1500 minutes.
12. The method according to embodiment 11, wherein in step (a) the first solvent mixture is incubated at about 30 minutes to about 120 minutes.
13. The method according to any one of embodiments 1-12, wherein step (a) is repeated at least once.
14. The method according to embodiment 13, wherein step (a) is repeated three times.
15. The method according to any one of embodiments 1-14, wherein in step (b), the volume of the first solvent mixture is reduced to about 1% to about 50% of the original volume of the first solvent mixture in step (a).
16. The method according to embodiment 15, wherein in step (b), the volume of the first solvent mixture is reduced to about 0.1% to about 15% of the original volume of the first solvent mixture in step (a).
17. The method according to embodiment 15, wherein in step (b), the volume of the first solvent mixture is reduced to about 16% to about 50% of the original volume of the first solvent mixture in step (a).
18. The method according to any one of embodiments 1-17, wherein in step (b), the volume of the first solvent mixture is reduced by evaporation.
19. The method according to any one of embodiments 1-18, wherein in step (c), the reduced first solvent mixture is incubated at a temperature range of between about −20° C. to about 30° C.
20. The method according to embodiment 19, wherein in step (c), the reduced first solvent mixture is incubated at a temperature range of between about 0° C. to about 25° C.
21. The method according to embodiment 20, wherein in step (c), the reduced first solvent mixture is incubated at a temperature range of between about 4° C. to about 8° C.
22. The method according to any one of embodiments 1-21, wherein in step (c), the reduced first solvent mixture is incubated for a time period of at least 30 minutes, at least 1 hour or at least 2 hours.
23. The method according to embodiment 22, wherein in step (c), the reduced first solvent mixture is incubated for a time period of between 1 hour and 96 hours.
24. The method according to embodiment 23, wherein in step (c), the reduced first solvent mixture is incubated for a time period of between 2 hour and 72 hours.
25. The method according to embodiment 24, wherein in step (c), the reduced first solvent mixture is incubated for a time period of between 4 hour and 48 hours.
26. The method according to embodiment 25, wherein in step (c), the reduced first solvent mixture is incubated for a time period of between 6 hour and 24 hours.

27. The method according to embodiment 26, wherein in step (c), the reduced first solvent mixture is incubated for a time period of between 12 hour and 24 hours.
28. The method according to any one of embodiments 1-27, wherein step (c) further comprises seeding the reduced solvent mixture with a cannabinoid.
29. The method according to embodiment 28, wherein the cannabinoid used to seed the reduced solvent mixture comprises a purified cannabinoid, a partially purified cannabinoid or crude extract comprising a cannabinoid.
30. The method according to any one of embodiments 1-29, wherein the second non-polar solvent of step (d) comprises pentane, hexane, heptane, petroleum ethers, cyclohexane, dichloromethane, trichloromethane, tetrahydrofurane, diethyl ether, toluene, benzene, ethanol, methanol, isopropanol, acetone, acetonitrile, ethyl acetate, butane, propane, refrigerant gases (e.g.: 1,1,1,2-Tetrafluoroethane (R134a)) or, liquid, subcritical or supercritical $CO_2$ or mixes of these solvents.
31. The method according to any one of embodiments 1-30, wherein in step (d), the second solvent mixture dissolves at least 75% of the one or more crystalized cannabinoids.
32. The method according to embodiment 31, wherein in step (d), the second solvent mixture dissolves at least 85% of the one or more crystalized cannabinoids.
33. The method according to embodiment 32, wherein in step (d), the second solvent mixture dissolves at least 95% of the one or more crystalized cannabinoids.
34. The method according to any one of embodiments 1-33, wherein in step (d), the second solvent mixture is incubated at a temperature range of between about 30° C. to about 60° C.
35. The method according to embodiment 34, wherein in step (d), the second solvent mixture is incubated at a temperature range of between about 40° C. to about 50° C.
37. The method according to any one of embodiments 1-35, wherein in step (d), the second solvent mixture is incubated for a time period of at least 6 minutes.
38. The method according to embodiment 37, wherein in step (d), the second solvent mixture is incubated for a time period of between 0.25 hour and 4 hours.
39. The method according to any one of embodiments 1-38, wherein in step (e), the second solvent mixture is incubated at a temperature range of between about −20° C. to about 30° C.
40. The method according to embodiment 39, wherein in step (e), the second solvent mixture is incubated at a temperature range of between about 0° C. to about 25° C.
41. The method according to embodiment 40, wherein in step (e), the second solvent mixture is incubated at a temperature range of between about 4° C. to about 8° C.
42. The method according to any one of embodiments 1-41, wherein in step (e), the second solvent mixture is incubated for a time period of at least 6 minutes, at least 1 hour, at least 2 hours, at least 3 hours or at least 4 hours.
43. The method according to embodiment 42, wherein in step (e), the second solvent mixture is incubated for a time period of between 0.1 hour and 96 hours.
44. The method according to embodiment 43, wherein in step (e), the second solvent mixture is incubated for a time period of between 2 hour and 72 hours.
45. The method according to embodiment 44, wherein in step (e), the second solvent mixture is incubated for a time period of between 4 hour and 48 hours.
46. The method according to embodiment 45, wherein in step (e), the second solvent mixture is incubated for a time period of between 6 hour and 24 hours.
47. The method according to embodiment 46, wherein in step (e), the second solvent mixture is incubated for a time period of between 12 hour and 24 hours.
48. The method according to any one of embodiments 1-47, wherein the one or more crystalized cannabinoids of step (c) is purified prior to step (d).
49. The method according to embodiment 48, wherein the purification is performed using filtration that results in a collection of a mother liquor.
50. The method according to embodiment 49, further comprising incubating the mother liquor at a temperature range of between about −70° C. to about 40° C. in a manner that crystalizes the one or more cannabinoids.
51. The method according to embodiment 50, further comprising f) purifying the one or more crystalized cannabinoids using filtration that results in a collection of a mother liquor; and g) incubating the mother liquor at a temperature range of between about −70° C. to about 40° C. in a manner that crystalizes the one or more cannabinoids.
52. The method according to any one of embodiments 1-52, wherein steps (f) and (g) are repeated at least once.
53. The method according to embodiment 52, wherein steps (f) and (g) are repeated 2 times.
54. The method according to embodiment 53, wherein steps (f) and (g) are repeated 3 times.
55. The method according to any one of embodiments 1-54, wherein steps (d) and (e) are repeated at least once.
56. The method according to embodiment 50, wherein steps (d) and (e) are repeated 2 times.
57. The method according to embodiment 51, wherein steps (d) and (e) are repeated 3 times.
58. The method according to any one of embodiments 1-57, wherein the first solvent mixture of step (a) is purified prior to step (b).
59. The method according to embodiment 58, wherein the purification is performed using filtration.
60. The method according to any one of embodiments 1-59, wherein the one or more crystalized cannabinoids of step (e) is filtered.
61. The method according to any one of embodiments 1-60, further comprising performing liquid:liquid chromatography after one or more of steps (b) or (d).
62. The method according to embodiment 61, wherein the liquid:liquid chromatography is counter current chromatography (CCC) or centrifugal partition chromatography (CPC).
63. The method according to embodiment 62, wherein the mobile organic phase includes pentane, hexane, cyclohexane, or heptane.
64. The method according to embodiment 62, wherein the stationary phase includes ethanol, methanol, isopropanol, acetone, acetonitrile and/or water.
65. The method according to embodiment 62, wherein the mobile phase is pentane, hexane, cyclohexane, or heptane and the stationary phase is water and ethanol, methanol, or isopropanol. In one embodiment, the two-phase system is hexane:ethanol:water at ratios of (20:19:1) to (20:8:12) and wherein hexane may be substituted by pentane, heptane and/or cyclohexane and wherein ethanol may be substituted by methanol and/or isopropanol instead of ethanol, with the organic phase of pentane or hexane as mobile phase or the two-phase system. In one embodiment the ratios of the two-phase system, hexane:ethanol:

water are (20:13:7) for CBG-type cannabinoids (20:14:6) for CBD-type cannabinoids and (20:17:3) for THC-type cannabinoids or using a gradient reverse phase run with ethanol and water mix as mobile phase increasing the concentration of ethanol gradually from the ratio (20:12:8) to (20:18:2).
66. The method according to embodiment 62, wherein the mobile phase is pentane, hexane or heptane with or without ethyl acetate as a modifier, and the stationary phase is acetone and/or acetonitrile with or without water as a modifier. In one embodiment the two phase system is pentane:acetonitrile or hexane:acetonitrile with or without ethyl acetate or water as a modifier, at ratios of (10:0:10:0) to (7:3:7:3). In one embodiment for THC-type cannabinoids the ratio of pentane:acetonitrile is from 10:10 (e.g., pentane:ethyl acetate:acetonitrile:water (10:0:10:0)) to 7:3:7:3 pentane:ethyl acetate:acetonitrile:water by volume. In another embodiment the ratio of hexane:acetonitrile is from 10:10 (e.g., hexane:ethyl acetate:acetonitrile:water (10:0:10:0)) to 7:3:7:3 hexane:ethyl acetate:acetonitrile:water by volume. Preferred solvent ratios for THC-type cannabinoids are pentane:ethyl acetate:acetonitrile:water at 19:1:19:1 by volume or 9:1:9:1 by volume.
67. A purified cannabinoid produced by the method according to any one of embodiments 1-66.
68. A pharmaceutical composition comprising a purified cannabinoid produced by the method according to any one of embodiments 1-66.
69. The pharmaceutical composition of embodiment 68, further comprising a pharmaceutically acceptable excipient or carrier.
70. A method of treating a disease or condition comprising administering the cannabinoid produced by the method according to any one of embodiments 1-66 to a subject in need thereof.
71. The method of treating a disease or condition of embodiment 70, wherein the disease or condition is pain, schizophrenia, convulsion, inflammation, anxiety, depression, neurodegenerative disease, stroke, traumatic brain injury, cancer, migraines, arthritis, chronic pain, nausea and vomiting, anorexia, glaucoma, epilepsy, asthma, addiction, symptoms of dependency and withdrawal, multiple sclerosis, spinal cord injury, Tourette's syndrome, dystonia, or tardive dyskinesia.
72. A method of purifying a cannabinoid from a plant material, the method comprising: a) incubating the plant material with a first non-polar solvent to form a first solvent mixture which extracts the one or more cannabinoids from a plant material; b) filtering the first solvent mixture; c) reducing the volume of the first solvent mixture to about 50% or less of the original volume of the first solvent mixture in step (a) in a manner that concentrates the one or more cannabinoids; d) incubating the reduced first solvent mixture at a temperature range of between about −70° C. to about 40° C. in a manner that crystallizes the one or more cannabinoids; e) purifying the one or more crystalized cannabinoids in step (d) using filtration that results in a collection of a mother liquor; f) incubating the one or more crystalized cannabinoids with a second non-polar solvent to form a second solvent mixture, wherein the second solvent mixture dissolves at least 50% of the one or more crystalized cannabinoids; g) incubating the second solvent mixture at a temperature range of between about −70° C. to about 40° C. in a manner that crystalizes the one or more cannabinoids; and h) purifying the one or more crystalized cannabinoids of step (g) using filtration that results in a collection of a mother liquor, thereby resulting in the purification of one or more cannabinoids
73. The method according to embodiment 72, wherein the mother liquor of step (e) and/or step (h) is incubated at a temperature range of between about −70° C. to about 40° C. in a manner that crystalizes the one or more cannabinoids.
74. The method according to embodiment 73, further comprising i) purifying the one or more crystalized cannabinoids using filtration that results in a collection of a mother liquor; and j) incubating the mother liquor at a temperature range of between about −70° C. to about 40° C. in a manner that crystalizes the one or more cannabinoids.
75. The method according to embodiment 74, wherein steps (i) and (j) are repeated at least once.
76. The method according to embodiment 75, wherein steps (i) and (j) are repeated 2 times.
77. The method according to embodiment 76, wherein steps (i) and (j) are repeated 3 times.
78. The method according to any one of embodiments 72-77, wherein steps (f) and (g) are repeated at least once.
79. The method according to embodiment 78, wherein steps (f) and (g) are repeated 2 times.
80. The method according to embodiment 79, wherein steps (f) and (g) are repeated 3 times.
81. The method according to any one of embodiments 72-80, wherein steps (f), (g) and (h) are repeated at least once.
82. The method according to embodiment 81, wherein steps (f), (g) and (h) are repeated 2 times.
83. The method according to embodiment 82, wherein steps (f), (g) and (h) are repeated 3 times.
84. The method according to any one of embodiments 72-83, wherein the plant material is a plant extract or a plant resin.
85. The method according to any one of embodiments 72-84, wherein the plaint material is derived from the genera *Cannabis*.
86. The method according to any one of embodiments 72-85, wherein the plaint material is derived from *Cannabis sativa* L., *Cannabis* indica *Cannabis ruderalis*, hybrids thereof or varietals thereof.
87. The method according to embodiment 86, wherein the *Cannabis sativa* L. varietal comprises a Chemotype II varietal, a Chemotype III varietal or a Chemotype IV varietal.
88. The method according to embodiment 86, wherein the *Cannabis sativa* L. varietal comprises a Carma varietal, a AIDA varietal, a SARA varietal, a PILAR varietal, a Futura 75, MONIEK varietal or a 60.2/1/9 experimental varietal.
89. The method according to any one of embodiments 72-88, wherein prior to step (a), the plant material is treated to decarboxylate one or more cannabinoids present in the plant material.
90. The method according to any one of embodiments 72-89, wherein the first non-polar solvent of step (a) comprises pentane, hexane, heptane, cyclohexane, petroleum ether, dicloromethane, tricloromethane, tethrahydrofurane, diethyl ether, benzene, toluene, ethanol, methanol, isopropanol, acetone, acetonitrile, ethyl acetate, butane, propane, refrigeration gas 1,1,1,2-Tetrafluoroethane (R134a), liquid $CO_2$, subcritical $CO_2$ and supercritical $CO_2$.
91. The method according to any one of embodiments 72-90, wherein the one or more cannabinoids comprise tetrahydrocannabinol (THC), tetrahydrocannabidivarin (THCV), tetrahidrocannabinolic acid (THCA), cannabidiol (CBD), cannabidivarin (CBDV), cannabidiolic acid (CBDA), cannabigerol (CBG), cannabigerovarin (CBGV) or cannabigerolic acid (CBGA).

92. The method according to any one of embodiments 72-91, wherein in step (a) the first solvent mixture is incubated at least 5 minutes.

93. The method according to embodiment 92, wherein in step (a) the first solvent mixture is incubated at about 10 minutes to about 1500 minutes.

94. The method according to embodiment 93, wherein in step (a) the first solvent mixture is incubated at about 30 minutes to about 120 minutes.

95. The method according to any one of embodiments 72-94, wherein step (a) is repeated at least once.

96. The method according to embodiment 95, wherein step (a) is repeated twice.

97. The method according to embodiment 96, wherein step (a) is repeated 3 times.

98. The method according to any one of embodiments 72-97, wherein in step (c), the volume of the first solvent mixture is reduced to about 5% to about 50% of the original volume of the first solvent mixture in step (a).

99. The method according to embodiment 98, wherein in step (c), the volume of the first solvent mixture is reduced to about 1% to about 15% of the original volume of the first solvent mixture in step (a).

100. The method according to embodiment 98, wherein in step (c), the volume of the first solvent mixture is reduced to about 15% to about 50% of the original volume of the first solvent mixture in step (a).

101. The method according to any one of embodiments 72-100, wherein in step (c), the volume of the first solvent mixture is reduced by evaporation.

102. The method according to any one of embodiments 72-101, wherein in step (d), the reduced first solvent mixture is incubated at a temperature range of between about −20° C. to about 30° C.

103. The method according to embodiment 102, wherein in step (d), the reduced first solvent mixture is incubated at a temperature range of between about 0° C. to about 25° C.

104. The method according to embodiment 103, wherein in step (d), the reduced first solvent mixture is incubated at a temperature range of between about 4° C. to about 8° C.

105. The method according to any one of embodiments 72-104, wherein in step (d), the reduced first solvent mixture is incubated for a time period of at least 30 minutes, at least 1 hour or at least 2 hours.

106. The method according to embodiment 105, wherein in step (d), the reduced first solvent mixture is incubated for a time period of between 1 hour and 96 hours.

107. The method according to embodiment 106, wherein in step (d), the reduced first solvent mixture is incubated for a time period of between 2 hour and 72 hours.

108. The method according to embodiment 107, wherein in step (d), the reduced first solvent mixture is incubated for a time period of between 4 hour and 48 hours.

109. The method according to embodiment 108, wherein in step (d), the reduced first solvent mixture is incubated for a time period of between 6 hour and 24 hours.

110. The method according to embodiment 109, wherein in step (d), the reduced first solvent mixture is incubated for a time period of between 12 hour and 24 hours.

111. The method according to any one of embodiments 72-110, wherein step (d) further comprises seeding the reduced solvent mixture with a cannabinoid.

112. The method according to embodiment 111, wherein the cannabinoid used to seed the reduced solvent mixture comprises a purified cannabinoid, a partially purified cannabinoid or crude extract comprising a cannabinoid.

113. The method according to any one of embodiments 72-112, wherein the second non-polar solvent of step (f) comprises pentane, hexane, heptane, cyclohexane, petroleum ether, dichloromethane, trichloromethane, tetrahydrofurane, diethyl ether, benzene, toluene, ethanol, methanol, isopropanol, acetone, acetonitrile, ethyl acetate, butane, propane, refrigeration gas 1,1,1,2-Tetrafluoroethane (R134a), liquid $CO_2$, subcritical $CO_2$ and supercritical $CO_2$.

114. The method according to any one of embodiments 72-113, wherein in step (f), the second solvent mixture dissolves at least 75% of the one or more crystalized cannabinoids.

115. The method according to embodiment 114, wherein in step (f), the second solvent mixture dissolves at least 85% of the one or more crystalized cannabinoids.

116. The method according to embodiment 115, wherein in step (f), the second solvent mixture dissolves at least 95% of the one or more crystalized cannabinoids.

117. The method according to any one of embodiments 72-116, wherein in step (f), the second solvent mixture is incubated at a temperature range of between about 30° C. to about 60° C.

118. The method according to embodiment 117, wherein in step (f), the second solvent mixture is incubated at a temperature range of between about 40° C. to about 50° C.

119. The method according to any one of embodiments 72-118, wherein in step (f), the second solvent mixture is incubated for a time period of at least 6 minutes.

120. The method according to embodiment 119, wherein in step (f), the second solvent mixture is incubated for a time period of between 0.1 hour and 4 hours.

121. The method according to any one of embodiments 72-120, wherein in step (g), the second solvent mixture is incubated at a temperature range of between about −20° C. to about 30° C.

122. The method according to embodiment 121, wherein in step (g), the second solvent mixture is incubated at a temperature range of between about 0° C. to about 25° C.

123. The method according to embodiment 122, wherein in step (g), the second solvent mixture is incubated at a temperature range of between about 4° C. to about 8° C.

124. The method according to any one of embodiments 72-123, wherein in step (g), the second solvent mixture is incubated for a time period of at least 6 minutes, at least 1 hour, at least 2 hours, at least 3 hours or at least 4 hours.

125. The method according to embodiment 124, wherein in step (g), the second solvent mixture is incubated for a time period of between 0.1 hour and 96 hours.

126. The method according to embodiment 125, wherein in step (g), the second solvent mixture is incubated for a time period of between 2 hour and 72 hours.

127. The method according to embodiment 126, wherein in step (g), the second solvent mixture is incubated for a time period of between 4 hour and 48 hours.

128. The method according to embodiment 127, wherein in step (g), the second solvent mixture is incubated for a time period of between 6 hour and 24 hours.

129. The method according to embodiment 128, wherein in step (g), the second solvent mixture is incubated for a time period of between 12 hour and 24 hours.

130. The method according to any one of embodiments 72-129, wherein the temperature in steps (d) and (g) is at most about 4° C. for CBGA/CBG purification and step (d) is at most −20° C. for CBD purification.
131. The method according to any one of embodiments 72-130, further comprising performing liquid:liquid chromatography after one or more of steps (c), (e) or (h).
132. The method according to embodiment 131, wherein the liquid:liquid chromatography is counter current chromatography (CCC) or centrifugal partition chromatography (CPC).
133. The method according to embodiment 131 or embodiment 132, wherein the mobile organic phase includes pentane, hexane, cyclohexane, or heptane.
134. The method according to any one of embodiments 131-132, wherein the stationary phase includes ethanol, methanol, isopropanol, acetone, acetonitrile and/or water.
135. The method according to embodiment 131 or embodiment 132, wherein the mobile phase is pentane, hexane, cyclohexane, or heptane and the stationary phase is water and ethanol, methanol, or isopropanol.
136. The method according to embodiment 131 or embodiment 132, wherein the mobile phase is pentane, hexane or heptane with or without ethyl acetate as a modifier, and the stationary phase is acetone and/or acetonitrile with or without water as a modifier.
137. The method according to any one of embodiments 72-136, further comprising performing counter current chromatography (CCC) or centrifugal partition chromatography (CPC) after the steps (e) or (h) to isolate, purify or repurify the cannabinoids tetrahydrocannabinol (THC), tetrahydrocannabidivarin (THCV), tetrahidrocannabinolic acid (THCA), tetrahydrocannabidivarinic acid (THCVA), cannabinol (CBN), cannabivarin (CBV) cannabidiol (CBD), cannabidivarin (CBDV), cannabidiolic acid (CBDA), cannabidivarinic acid (CBDVA), cannabigerol (CBG), cannabigerovarin (CBGV), cannabigerovarinic acid (CBGVA) and cannabigerolic acid (CBGA).
138. The method according to any one of embodiments 131-137, wherein the chromatography uses a two-phase system, hexane:ethanol:water at ratios of (20:19:1) to (20:8:12) and wherein hexane may be substituted by pentane, heptane and/or cyclohexane and wherein ethanol may be substituted by methanol and/or isopropanol instead of ethanol, with the organic phase of pentane or hexane as mobile phase or the two-phase system. The chromatography also uses a two phase system pentane: acetonitrile or hexane:acetonitrile with or without ethyl acetate or water as a modifier, at ratios of (10:0:10:0) to (7:3:7:3).
139. The method according to any one of embodiments 131-138, wherein the ratios of the two-phase system, hexane:ethanol:water are (20:13:7) for CBG-type cannabinoids (20:14:6) for CBD-type cannabinoids and (20:17:3) for THC-type cannabinoids or using a gradient reverse phase run with ethanol and water mix as mobile phase increasing the concentration of ethanol gradually from the ratio (20:12:8) to (20:18:2). For THC-type extracts the ratio of pentane:acetonitrile is from 10:10 (e.g., pentane:ethyl acetate:acetonitrile:water (10:0:10:0)) to 7:3:7:3 pentane:ethyl acetate:acetonitrile:water by volume. In another embodiment the ratio of hexane:acetonitrile is from 10:10 (e.g., hexane:ethyl acetate:acetonitrile: water (10:0:10:0)) to 7:3:7:3 hexane:ethyl acetate: acetonitrile:water by volume. Preferred solvent ratios for THC-type cannabinoids are pentane:ethyl acetate:acetonitrile:water at
19:1:19:1 by volume or 9:1:9:1 by volume.
140. The method according to any one of embodiments 72-139, wherein cannabigerol (CBG), cannabigerovarin (CBGV), cannabidiol (CBD), cannabidivarin (CBDV), cannabivarin (CBV), cannabinol (CBN), tetrahydrocannabidivarin (THCV) or tetrahidrocannabinol (THC) are isolated and purified and prior to step (a), the plant material, resin or extracts of said plant are decarboxylated at about at least 120° C. for at least 1 hour.
141. The method according to any one of embodiments 72-139, wherein cannabigerol (CBG), cannabigerovarin (CBGV), cannabidiol (CBD), cannabidivarin (CBDV), cannabivarin (CBV), cannabinol (CBN), tetrahydrocannabidivarin (THCV) or tetrahidrocannabinol (THC) is isolated and purified, and prior to step (a), the plant, plant material, plant extract, or resin are decarboxylated by hydrodistillation (steem distillation) at least at 90° C. for 2 hours.
142. A purified cannabinoid produced by the method according to any one of embodiments 72-141.
143. A pharmaceutical composition comprising a purified cannabinoid produced by the method according to any one of embodiments 72-141.
144. The pharmaceutical composition of embodiment 143, further comprising a pharmaceutically acceptable excipient or carrier.
145. A method of treating a disease or condition comprising administering the cannabinoid produced by the method according to any one of embodiments 72-141 to a subject in need thereof.
146. The method of treating a disease or condition of embodiment 145, wherein the disease or condition is pain, schizophrenia, convulsion, inflammation, anxiety, depression, neurodegenerative disease, stroke, traumatic brain injury, cancer, migraines, arthritis, chronic pain, nausea and vomiting, anorexia, glaucoma, epilepsy, asthma, addiction, symptoms of dependency and withdrawal, multiple sclerosis, spinal cord injury, Tourette's syndrome, dystonia, or tardive dyskinesia.
147. The method according to any one of embodiments 7 or 89, wherein the plant material is heated between 100° C. to 160° C. in order to decarboxylate one or more cannabinoids present in the plant material.
148. The method according to embodiment 147, wherein the plant material is heated between 120° C. to 150° C. in order to decarboxylate one or more cannabinoids present in the plant material.
149. The method according to embodiments 147 or 148, wherein the plant material is heated for a time period of at least 30 minutes.
150. The method according to embodiment 149, wherein the plant material is heated for a time period of about 1 hour to about 3 hours.
151. The method according to any one of embodiments 1-150, wherein the one or more cannabinoids purified is CBGA, CBG, CBGV, CBDA, CBD, CBDV, THCA, THC, THCV or any combination thereof.
152. The method according to embodiments 151, wherein the CBGA has a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

153. The method according to embodiments 151, wherein the CBG, CBGA or CBGV has a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

154. The method according to embodiments 151, wherein the CBD, CBDA or CBDV has a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

155. The method according to embodiments 151, wherein the THC, THCA, or THCV has a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

156. The pharmaceutical composition of any one of embodiments 68, 69, 143 or 144, wherein the purified cannabinoid is CBG, CBGA, CBGV, CBD, CBDA, CBDV, THC, THCA, or THCV or any combination thereof.

157. The pharmaceutical composition of embodiment 156, wherein the purified cannabinoid is CBGA or CBGV having a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

158. The pharmaceutical composition of embodiment 156, wherein the purified cannabinoid is CBG having a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

159. The pharmaceutical composition of embodiment 156, wherein the purified cannabinoid is THC, THCA or THCV having a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

160. The pharmaceutical composition of embodiment 156, wherein the purified cannabinoid is CBD, CBDA, or CBDV having a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

161. The method according to any one of embodiments 1-155, wherein a substantially pure preparation of one or more cannabinoids is achieved without the use a chromatographic technique.

162. The method according to embodiment 161, wherein a substantially pure preparation of CBGA or CBGV is achieved without the use a chromatographic technique.

163. The method according to embodiment 161, wherein a substantially pure preparation of CBG is achieved without the use a chromatographic technique.

164. The method according to embodiment 161, wherein a substantially pure preparation of CBD, CBDA, or CBDV is achieved without the use a chromatographic technique.

165. The method according to embodiment 161, wherein a substantially pure preparation of THC, THCA or THCV is achieved without the use a chromatographic technique.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1

Purification of Cannabinoids CBD and CBDV Using Centrifugation Partitioning Chromatography Maceration of 100 g of plant material of the variety Theresa with CBD/CBDV was carried out in 1 L of petroleum ether (40-60° C. bp) for one hour. This procedure was repeated two times with 0.75 L of petroleum ether (40-60° C. bp). The plant material was filtered, and the petroleum ether evaporated down completely to achieve 9.1 g of dry extract. This 9.1 g of extract was decarboxylated at 150° C. for 2 hours obtaining 8.7 g of decarboxylated extract. 8 g of the extract was dissolved with hexane at a volume of 50 mL and then used as a sample for injection in the CPC 1000 PRO (Gilson) before called CPC-Quantum (Armen) of 1 L rotor volume. We use the biphasic solvent system hexane:ethanol:water at proportions of 20:14:6, the flow rate of the mobile phase (hexane phase) is 200 mL/min during the run, and changed to 350 mL/min in the extrusion and change of the stationary phase (ethanolic phase). The complete run last 14 minutes, with 2 phases: run with pumping mobile phase that is from 10 minutes and an extrusion phase of 4 minutes. The use of solvent per run is from 2 L of hexane and 1.4 L of Ethanolic phase. The total solvent used is from 3.4 L per run. We obtain 2.9 g of CBD in the fraction from minute 4:55 to 7:20 and 0.9 g of CBDV in the fraction from the minute 7:20 to 10. The purity of the evaporated fractions was >95% after recrystallization in petroleum ether (40-60° C. bp) the CBD or after wash or recrystallization in petroleum ether (40-60° C. bp) or hexane from the CBDV.

Example 2

Purification of Cannabinoids CBD and CBDA Using Centrifugation Partitioning Chromatography Maceration of 100 g of plant material of the variety Sara with CBDA was carried out in 1 L of petroleum ether (40-60° C. bp) for one hour. This procedure was repeated two times with 0.75 L of petroleum ether (40-60° C. bp). The plant material was filtered, and the petroleum ether evaporated down completely to achieve 15 g of dry extract. 8 g of the extract was dissolved with hexane at a volume of 50 mL and then used as a sample for injection in the CPC 1000 PRO (Gilson) before called CPC-Quantum (Armen) of 1 L rotor volume. We use the biphasic solvent system hexane:ethanol:water at proportions of 20:14:6, the flow rate of the mobile phase (hexane phase) is 200 mL/min during the run, and changed to 350 mL/min in the extrusion and change of the stationary phase (ethanolic phase). The complete run last 15 minutes, with 2 phases: run with pumping mobile phase that is from 11 minutes and an extrusion phase of 4 minutes. The use of solvent per run is from 2.2 L of hexane and 1.4 L of Ethanolic phase. The total solvent used is from 3.6 L per run. We obtain 0.7 g of CBD in the fraction from minute 5:31 to 7.20 and 3.7 g of CBDV in the fraction from the minute 7.20 to 11. The purity of the evaporated fractions was >95% after dryness of the CBDA and after recrystallization in petroleum ether (40-60° C. bp) the CBD.

Example 3

Purification of Cannabinoids CBG and CBGV Using Counter Currentt Chromatography

Maceration of 100 g of plant material of the variety Juani with CBG/CBGV was carried out in 1 L of hexane for one hour. This procedure was repeated two times with 0.75 L of hexane. The plant material was filtered, and the hexane evaporated down completely to achieve 6 g of dry extract. This 6 g of extract was decarboxylated at 150° C. for 2 hours obtaining 5.6 g of decarboxylated extract. 3.5 g of the extract was dissolved with hexane at a volume of 20 mL and then used as a sample for injection in the LabPrep CCC (AECS) in the coil of 750 mL and 2.8 mm I.D. We use the biphasic solvent system hexane:ethanol:water at proportions of 20:12:8, the flow rate of the mobile phase (hexane phase) is 25 mL/min during the run, and changed to 35 mL/min in the extrusion and change of the stationary phase (ethanolic phase). The complete run last 75 minutes, with 2 phases: run with pumping mobile phase that last 60 minutes and an extrusion phase of 25 minutes. The use of solvent per run is from 1.5 L of hexane and 0.875 L of Ethanolic phase. The total solvent used is from 2.375 L per run. We obtain 0.7 g of CBG in the fraction from minute 20 to 31 and 3.7 g of CBGV in the fraction from the minute 45 to 57. The fraction from minute 32 to 45 contains 0.1 g of a mixture of CBG/CBGV. The purity of the evaporated fractions was >95% after dryness of the CBGV and after recrystallization in hexane for the CBG. CBGV was easily recrystallized in hexane in order to obtain higher purity.

Example 4

Purification of Cannabinoids THCA and THC Using Counter Current Chromatography

Maceration of 100 g of plant material of the variety Moniek with THC/THCA was carried out in 1 L of hexane for one hour. This procedure was repeated two times with 0.75 L of hexane. The plant material was filtered, and the hexane evaporated down completely to achieve 26 g of dry extract. This 26 g of extract was decarboxylated at 120° C. for 2 hours obtaining 24 g of decarboxylated extract. 2 g of the extract was dissolved with hexane at a volume of 20 mL and then used as a sample for injection in the LabPrep CCC (AECS) in the coil of 750 mL and 2.8 mm I.D. We use the biphasic solvent system hexane:ethanol:water at proportions of 20:17:3, the flow rate of the mobile phase (hexane phase) is 25 mL/min during the run, and changed to 35 mL/min in the extrusion and change of the stationary phase (ethanolic phase). The complete run last 70 minutes, with 2 phases: run with pumping mobile phase that last 45 minutes and an extrusion phase of 25 minutes. The use of solvent per run is from 1.125 L of hexane and 0.875 L of Ethanolic phase. The total solvent used is from 2 L per run. We obtain 0.8 g of THCA in the fraction from minute 30 to 35 and 0.25 g of THC in the fraction from the minute 38 to 43. The fraction from minute 35 to 38 contains 0.2 g of a mixture of THCA/THC. The purity of the evaporated fractions was >95% after dryness. THCA can be recrystallized in heptane in order to increase the purity at higher percentages.

Example 5

Purification of Cannabinoids THC, THCV and CBV (CBNV) Using Counter Current Chromatography Maceration of 100 g of plant material of the experimental breeding cross pollinated 60.1/4/4/8×51.2/8/2 with THC/THCV was carried out in 1 L of hexane for one hour. This procedure was repeated two times with 0.75 L of hexane. The plant material was filtered, and the hexane evaporated down completely to achieve 9 g of dry extract. This 9 g of extract was decarboxylated at 120° C. for 2 hours obtaining 7.9 g of decarboxylated extract. 1.5 g of the extract was dissolved with hexane at a volume of 20 mL and then used as a sample for injection in the LabPrep CCC (AECS) in the coil of 750 mL and 2.8 mm I.D. We use the biphasic solvent system hexane:ethanol:water at proportions of 20:17:3, the flow rate of the mobile phase (hexane phase) is 25 mL/min during the run, and changed to 35 mL/min in the extrusion and change of the stationary phase (ethanolic phase). The complete run last 75 minutes, with 2 phases: run with pumping mobile phase that last 50 minutes and an extrusion phase of 25 minutes. The use of solvent per run is from 1.250 L of hexane and 0.875 L of Ethanolic phase. The total solvent used is from 2.125 L per run. We obtain 0.6 g of THC in the fraction from minute 22 to 27 and 0.15 g of THCV in the fraction from the minute 32 to 38. The fraction from minute 27 to 32 contains 0.1 g of a mixture of THC/THCV. The fraction from minute 40 to 48 contains 0.035 g of CBV. The purity of the evaporated fractions was >95% after dryness.

Example 6

Purification of Cannabinoids THC+THCV Using Counter Current Chromatography

Maceration of 100 g of plant material of the experimental breeding cross pollinated 60.1/4/4/8×51.2/8/2 with THC/THCV was carried out in 1 L of hexane for one hour. This procedure was repeated two times with 0.75 L of hexane. The plant material was filtered, and the hexane evaporated down completely to achieve 9 g of dry extract. This 9 g of extract was decarboxylated at 120° C. for 2 hours obtaining 7.9 g of decarboxylated extract. 0.5 g of the extract was dissolved with hexane at a volume of 5 mL and then used as a sample for injection in the LabPrep CCC (AECS) in the coil of 155 mL and 0.8 mm I.D. We use the biphasic solvent system hexane:acetonitrile at proportions of 10:10, the flow rate of the mobile phase (hexane phase) is 8 mL/min during the run, and changed to 15 mL/min in the extrusion and change of the stationary phase (acetonitrile phase). The complete run last 102 minutes, with 2 phases: run with pumping mobile phase that last 90 minutes and an extrusion phase of 12 minutes. The use of solvent per run is from 0.720 L of hexane and 0.180 L of acetonitrile phase. The total solvent used is from 0.9 L per run. We obtain 0.2 g of THC in the fraction from minute 45 to 58 and 0.057 g of THCV in the fraction from the minute 65 to 83. The fraction from minute 59 to 64 contains 0.01 g of a mixture of THC/THCV+CBCV. The fraction from minute 39 to 45 contains 0.04 g of THC+CBC. The purity of the evaporated fractions that contain one cannabinoid was >95% after dryness.

Example 7

Purification of Cannabinoids THC+THCV Using Counter Current Chromatography

Maceration of 100 g of plant material of the experimental breeding cross pollinated 60.1/4/4/8×51.2/8/2 with THC/THCV was carried out in 1 L of hexane for one hour. This procedure was repeated two times with 0.75 L of hexane. The plant material was filtered, and the hexane evaporated down completely to achieve 9 g of dry extract. This 9 g of extract was decarboxylated at 120° C. for 2 hours obtaining 7.9 g of decarboxylated extract. 0.5 g of the extract was dissolved with hexane at a volume of 5 mL and then used as a sample for injection in the LabPrep CCC (AECS) in the coil of 155 mL and 0.8 mm I.D. We use the biphasic solvent system hexane:ethyl Acetate:acetonitrile:water at proportions of 9:1:9:1, the flow rate of the mobile phase (hexane phase) is 8 mL/min during the run, and changed to 15 mL/min in the extrusion and change of the stationary phase (acetonitrile phase). The complete run last 72 minutes, with 2 phases: run with pumping mobile phase that last 60 minutes and an extrusion phase of 12 minutes. The use of solvent per run is from 0.480 L of hexane:ethyl acetate and 0.180 L of acetonitrile:water phase. The total solvent used is from 0.660 L per run. We obtain 0.21 g of THC in the fraction from minute 22 to 37 and 0.051 g of THCV in the fraction from the minute 47 to 58. The fraction from minute 38 to 46 contains 0.01 g of a mixture of THC/THCV. The purity of the evaporated fractions that contain one cannabinoid was >95% after dryness.

Example 8

Purification of Cannabinoids THC and THCA Using Centrifugation Partitioning Chromatography Maceration of 100 g of plant material of the variety Moniek with THC/THCA was carried out in 1 L of hexane for one hour. This procedure was repeated two times with 0.75 L of hexane. The plant material was filtered, and the hexane evaporated down completely to achieve 26 g of dry extract. This 26 g of extract was decarboxylated at 120° C. for 2 hours obtaining 24 g of decarboxylated extract. 5 g of the extract was dissolved with hexane at a volume of 50 mL and then used as a sample for injection in the CPC 1000 PRO (Gilson) before called CPC-Quantum (Armen) of 1 L rotor volume. We use the biphasic solvent system hexane:ethanol:water at proportions of 20:14:6, the flow rate of the mobile phase (hexane phase) is 200 mL/min during the run, and changed to 350 mL/min in the extrusion and change of the stationary phase (ethanolic phase). The complete run last 13 minutes, with 2 phases: run with pumping mobile phase that is from 9 minutes and an extrusion phase of 4 minutes. The use of solvent per run is from 1.8 L of hexane and 1.4 L of Ethanolic phase. The total solvent used is from 3.2 L per run. We obtain 2.9 g of THCA in the fraction from minute 4.45 to 5.40 and 0.7 g of a mixture of THCA/THC in the fraction from the minute 5.40 to 7.20. The purity of the evaporated fractions was >95% after dryness of the THCA.

Example 9

Purification of Cannabinoids THC and THCV Using Centrifugation Partitioning Chromatography Maceration of 100 g of plant material of the variety Raquel with THC/THCV was carried out in 1 L of hexane for one hour. This procedure was repeated two times with 0.75 L of hexane. The plant material was filtered, and the hexane evaporated down completely to achieve 16 g of dry extract. This 16 g of extract was decarboxylated at 120° C. for 2 hours obtaining 14 g of decarboxylated extract. 4 g of the extract was dissolved with hexane at a volume of 50 mL and then used as a sample for injection in the CPC 1000 PRO (Gilson) before called CPC-Quantum (Armen) of 1 L rotor volume. We use the biphasic solvent system hexane:ethanol:water at proportions of 20:14:6, the flow rate of the mobile phase (hexane phase) is 200 mL/min during the run, and changed to 350 mL/min in the extrusion and change of the stationary phase (ethanolic phase). The complete run last 15 minutes, with 2 phases: run with pumping mobile phase that is from 11 minutes and an extrusion phase of 4 minutes. The use of solvent per run is from 2.2 L of hexane and 1.4 L of Ethanolic phase. The total solvent used is from 3.6 L per run. We obtain 2.4 g of THC in the fraction from minute 6.25 to 7.25 and 0.42 g of THCV in the fraction from the minute 8.10 to 9.00. The purity of the evaporated fractions was >95% after dryness of the THC and THCV. The 14 g of extract were purified with 3 run of CPC obtaining 7.2 g of THC>95% purity and 1.25 g of THCV>95% purity.

1 g of the fraction pool from minute 7.23 to 8.09 of the 3 anterior run, a mix of THC, THCV and CBN, was purified by flash chromatography over a 120 g column of C18 bounded silica with water:acetronitrile as a mobile phase in gradient mode at a 40 mL/min flow.

| TIME (min) | % Water (10% acetonitrile) | % Acetonitrile (10% water) |
|---|---|---|
| 0 | 35 | 65 |
| 11 | 15 | 85 |
| 20 | 0 | 100 |
| 28 | 0 | 100 |
| 28.1 | 35 | 65 |

The total run was 28 minutes and the total solvent use was 1.12 L. We obtain 0.3 g of THCV in the fraction from minute 20.00 to 22.00, 0.2 g of CBN in the fraction from the minute 22.00 to 24.00 and 0.32 g of THC in the fraction from the minute 24.00 to 28.00. The purity of the evaporated fractions was >95% after dryness of the THCV and THC.

To further purify the THC fraction, 1.2 g of the THC with purity >90% but contaminated with CBC was purified with flash chromatography on a column of 120 g of C18 bounded silica using a acetonitrile:water in gradient mode and a mobile phase at flow of 40 ml/min.

| TIME (min) | % Water (10% acetonitrile) | % Acetonitrile (10% water) |
|---|---|---|
| 0 | 35 | 65 |
| 11 | 15 | 85 |
| 20 | 0 | 100 |
| 30 | 0 | 100 |
| 30.1 | 35 | 65 |

The total run was 30.1 minutes and the total solvent use was 1.2 L. We obtain 1.1 g of THC in the fraction from minute 24.00 to 28.00 and 0.05 g of CBC in the fraction from the minute 22.00 to 24.10. The purity of the evaporated fraction was >97.5% after dryness of the THC. 5 injections of 1.2 g were made in the same 120 g column of C18 bounded silica obtaining 5.4 g of THC>97.5% purity.

Example 10

Purification of Cannabinoids THC and THCV Using Centrifugation Partitioning Chromatography Maceration of 100 g of plant material of the variety Raquel with THC/THCV was carried out in 1 L of hexane for one hour. This procedure was repeated two times with 0.75 L of hexane. The plant material was filtered, and the hexane evaporated down completely to achieve 16 g of dry extract. This 16 g of extract was decarboxylated at 120° C. for 2 hours obtaining 14 g of decarboxylated extract. 5 g of the extract was dissolved with hexane at a volume of 50 mL and then used as a sample for injection in the CPC 1000 PRO (Gilson) before called CPC-Quantum (Armen) of 1 L rotor volume. We use the biphasic solvent system hexane:acetonitrile at proportions of 1:1, the flow rate of the mobile phase (hexane phase) is 200 mL/min during the run, and changed to 350 mL/min in the extrusion and change of the stationary phase (acetonitrile phase). The complete run last 31 minutes, with 2 phases: run with pumping mobile phase that is from 25 minutes and an extrusion phase of 4 minutes. The use of solvent per run is from 5.0 L of hexane and 1.4 L of acetonitrile phase. The total solvent used is from 6.4 L per run. We obtain 2.3 g of THC in the fraction from minute 13.23 to 17.30 and 0.51 g of THCV in the fraction from the minute 21.55 to 24.10. The purity of the evaporated fractions was >95% after dryness of the THC and THCV.

Example 11

Purification of Cannabinoids THC and THCV Using Centrifugation Partitioning Chromatography Maceration of 100 g of plant material of the variety Raquel with THC/THCV was carried out in 1 L of hexane for one hour. This procedure was repeated two times with 0.75 L of hexane. The plant material was filtered, and the hexane evaporated down completely to achieve 16 g of dry extract. This 16 g of extract was decarboxylated at 120° C. for 2 hours obtaining 14 g of decarboxylated extract. 5 g of the extract was dissolved with hexane at a volume of 50 mL and then used as a sample for injection in the CPC 1000 PRO (Gilson) before called CPC-Quantum (Armen) of 1 L rotor volume. We use the biphasic solvent system hexane:ethyl acetate:acetonitrile:water at proportions of 9:1:9:1, the flow rate of the mobile phase (hexane:ethyl acetate phase) is 200 mL/min during the run, and changed to 350 mL/min in the extrusion and change of the stationary phase (acetonitrile:water phase). The complete run last 21 minutes, with 2 phases: run with pumping mobile phase that is from 17 minutes and an extrusion phase of 4 minutes. The use of solvent per run is from 3.4 L of hexane:ethyl acetate phase and 1.4 L of acetonitrile:water phase. The total solvent used is from 4.8 L per run. We obtain 2.0 g of THC in the fraction from minute 13.23 to 17.30 and 0.40 g of THCV in the fraction from the minute 21.55 to 24.10. The purity of the evaporated fractions was >95% after dryness of the THC and >90% of the THCV. The 14 g of extract was purified by 3 runs of CPC obtaining 1.2 g of THCV fraction.

To further purify the THCV fraction, 1.2 g of the THCV with purity >90% but contaminated with CBN was purified with flash chromatography on a column of 120 g of C18 silica using a acetonitrile:water in gradient mode and a mobile phase at flow of 40 ml/min.

| TIME (min) | % Water (10% acetonitrile) | % Acetonitrile (10% water) |
|---|---|---|
| 0 | 35 | 65 |
| 11 | 15 | 85 |
| 20 | 0 | 100 |
| 24 | 0 | 100 |
| 24.1 | 35 | 65 |

The total run was 24 minutes and the total solvent use was 0.96 L. We obtain 0.84 g of THCV in the fraction from minute 20.00 to 22.00 and 0.40 g of CBN in the fraction from the minute 22.00 to 24.10. The purity of the evaporated fraction was >95% after dryness of the THCV.

The starting material is *cannabis* extract (whatever solvent is used in the production of the extract) and if it is decarboxylated or not, even if it is "winterized" (solved in ethanol, chilled at 4° C. or −20° C. and filtered from the precipitated material) or not.

We use different proportions of the solvents in the biphasic solvent system depending of which cannabinoid we want to purify: To purify THC, THCA, THCV, THCVA, CBN or CBV we use the biphasic system hexane:ethanol:water at proportions of 20:17:3 in volume or pentane:acetonitrile or hexane:acetonitrile with or without the use of ethyl acetate and or water as modifiers. To purify CBD, CBDA, CBDVA and/or CBDV we use the biphasic system hexane:ethanol:water at proportions of 20:14:6 in volume. To purify CBG, CBGA, CBGVA and/or CBGV we use the biphasic system hexane:ethanol:water at proportions of 20:12:8 in volume.

We use a CPC-Quantum (ARMEN) or CPC 1000 PRO (GILSON) of 1 L rotor volume, the sample injection is 50 mL (the g of extract depends on extract type and solvent system used), the flow rate of the mobile phase (hexane or pentane phase) is 200 mL/min during the run, and changed to 350 mL/min in the extrusion and change of the stationary phase (ethanolic or acetonitrile phase). The complete run varies from 12 to 31 minutes, with 2 phases: run with pumping mobile phase that is from 8 to 27 minutes and an extrusion phase of 4 minutes. The use of solvent per run is from 1.6 to 5.4 L of hexane phase and 1.4 L of ethanolic or acetonitrile phase. The total solvent used is from 3 to 6.8 per run.

Using extracts with the main cannabinoid at 40% to 60% the maximum load of a THC-Type extract is 5 g/L of rotor. The maximum load for a CBD-Type extract is 12 g/L of rotor. The maximum load for CBG-Type extract is 15 g/L of rotor.

Using extracts with the main cannabinoid at 40% to 60% the maximum recovery or yield of a THC-Type extract in pure cannabinoid is 2.8 g/run. The maximum recovery or yield of a CBD-Type extract is 6 g/run. The maximum recovery or yield of a CBG-Type extract is 7 g/L of rotor.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method of purifying one or more cannabinoids from a plant material including a plant, a plant resin or a plant extract, the method consisting essentially of the following steps:
   (a) incubating the plant material with a solvent selected from the group consisting of pentane, hexane, heptane, petroleum ethers, cyclohexane, dichloromethane, trichloromethane, tetrahydrofuran, diethyl ether, toluene, benzene, ethanol, methanol, isopropanol, acetone, acetonitrile, ethyl acetate, butane, propane, 1,1,1,2-Tetrafluoroethane (R134a) or, liquid, subcritical or supercritical $CO_2$ or mixes thereof to form a solvent mixture which extracts the one or more cannabinoids from the plant material, wherein the solvent mixture has an original volume;
   (b) for THC-type extracts, adding to the solvent mixture a biphasic solvent system selected from the group consisting of hexane:ethanol:water, pentane:acetonitrile and hexane:acetonitrile, wherein the pentane:acetonitrile system and the hexane:acetonitrile system optionally include ethyl acetate and/or water as a modifier; for CBD-type extracts, adding to the extract a biphasic solvent system of hexane:ethanol:water; and for CBG-type extracts, adding to the extract a biphasic solvent system of hexane:ethanol:water; and
   (c) performing liquid:liquid chromatography using a biphasic solvent system of step b), thereby purifying the one or more cannabinoids,
wherein fractions of tetrahydrocannabinol (THC) contaminated by cannabichromene (CBC) or fractions of tetrahydrocannabivarin (THCV) contaminated with cannabinol (CBN) are re-purified using solid-liquid chromatography selected from the group consisting of gravity, Flash or preparative HPLC over C-8 or C-18 coated silica solid stationary phase, using a gradient of acetonitrile:water mobile liquid phase.

2. The method of claim 1, wherein for the THC-type extracts the biphasic solvent system is hexane:ethanol:water is at a ratio of (20:17:3) by volume.

3. The method of claim 1, wherein for the THC-type extracts the biphasic solvent system is pentane:ethyl acetate:acetonitrile:water or hexane:ethyl acetate:acetonitrile:water at a ratio from (10:0:10:0) to (7:3:7:3) by volume.

4. The method of claim 1, wherein for the CBD-type extracts the biphasic solvent system is hexane:ethanol:water at a ratio of (20:14:6) by volume.

5. The method of claim 1, wherein for the CBG-type extracts the biphasic solvent system is hexane:ethanol:water at a ratio of (20:12:8) or (20:13:7) by volume.

6. The method of claim 1, wherein an extract of chemotype I or II Cannabis sativa L. is used to purify THC, THCA, THCV, THCVA, CBN or CBV and fractionate the CBD-type and CBG-type cannabinoids.

7. The method of claim 1, wherein an extract of chemotype II or III Cannabis sativa L. is used to purify CBD, CBDA, CBDVA or CBDV and fractionate the THC-type and CBG-type cannabinoids.

8. The method of claim 1, wherein an extract of chemotype IV Cannabis sativa L. is used to purify CBG, CBGA, CBGVA or CBGV and fractionate the CBD-type and THC-type cannabinoids.

9. The method of claim 1, wherein the liquid:liquid chromatography is centrifugation partitioning chromatography (CPC) or is counter current chromatography (CCC).

10. The method of claim 1, wherein after step a) the solvent mixture is reduced to dryness or to about 50% or less of the original volume of the solvent mixture in step (a) thereby concentrating the one or more cannabinoids before the liquid:liquid chromatography.

11. The method according to claim 1, wherein the solvent mixture of step (a) is purified prior to step (b).

12. The method according to claim 1, wherein prior to step (a), the one or more cannabinoids present in the plant material are decarboxylated by heating the plant material.

13. The method of claim 10, wherein after the solvent mixture is reduced to dryness, a dry extract product of the solvent mixture is dissolved in ethanol, chilled at a temperature from −20° C. to 4° C., filtered to remove precipitated material and reduced to dryness before purification by liquid-liquid chromatography.

14. The method of claim 9, using a rotor design Quantum CPC or CPC PRO, wherein the total run time is 12-20 minutes, independent of rotor volume.

15. The method of claim 7, wherein the CBD, CBDA, CBDVA or CBDV is crystalized after the step of liquid:liquid chromatography.

16. The method of claim 8, wherein the CBG, CBGA, CBGVA or CBGV is crystalized after the step of liquid:liquid chromatography.

17. The method of claim 1, wherein in step (a) the plant material is incubated with a non-polar solvent selected from the group consisting of petroleum ether, pentane, hexane and heptane to form a solvent mixture which extracts the one or more cannabinoids from the plant material to form the solvent mixture.

18. The method of claim 1, wherein the plant material is first incubated with a solvent selected from the group consisting of pentane, hexane, heptane, petroleum ethers, cyclohexane, dichloromethane, trichloromethane, tetrahydrofuran, diethyl ether, toluene, benzene, ethanol, methanol, isopropanol, acetone, acetonitrile, ethyl acetate, butane, propane, 1,1,1,2-Tetrafluoroethane (R134a) or, liquid, subcritical or supercritical $CO_2$ or mixes thereof; filtered, decanted or centrifuged; reduced to dryness; and then incubated with a non-polar solvent selected from the group consisting of petroleum ether, pentane, hexane and heptane to form a solvent mixture which extracts the one or more cannabinoids from the plant material to form the solvent mixture.

19. The method of claim 14, wherein the rotor has a rotor volume of 1 liter, a sample injection of 50 mL, a flow rate of a mobile phase (pentane or hexane phase) of the biphasic solvent system of 200 mL/min during the run, and a flow rate of a stationary phase (the ethanolic or acetonitrile phase) of the biphasic solvent system of 350 mL/min during the extrusion phase of the run.

* * * * *